US005750372A

United States Patent [19]
Sakai et al.

[11] Patent Number: 5,750,372
[45] Date of Patent: May 12, 1998

[54] VECTOR HAVING PROMOTER THAT IS INDUCIBLE BY METHANOL AND/OR GLYCEROL

[75] Inventors: Yasuyoshi Sakai, Shiga-ken; Yoshiki Tani, Kyoto; Yuji Shibano, Osaka; Hiroto Kondo; Haruyo Hatanaka, both of Kyoto, all of Japan

[73] Assignee: Suntory Limited, Osaka, Japan

[21] Appl. No.: 485,284

[22] Filed: Jun. 7, 1995

Related U.S. Application Data

[63] Continuation of Ser. No. 25,416, Mar. 1, 1993, abandoned.

[30] Foreign Application Priority Data

Feb. 28, 1992 [JP] Japan ................... 4-043361

[51] Int. Cl.$^6$ .................. C12P 21/06; C12N 1/19; C12N 15/81; C12N 15/11
[52] U.S. Cl. .................. 435/69.1; 435/192; 435/194; 435/320.1; 435/254.2; 536/23.1; 536/23.2; 536/23.7; 536/24.1
[58] Field of Search .................. 435/320.1, 69.1, 435/71.1, 71.2, 71.3, 192, 172.3, 194, 254.2; 536/23.1, 23.7, 24.1, 23.2

[56] References Cited

FOREIGN PATENT DOCUMENTS 0183071  6/1986  European Pat. Off. .
043822   7/1991  European Pat. Off. .

OTHER PUBLICATIONS

Sreekrishna et al., High Level Expression of Heterologous Proteins in Methylotrophic Yeast Pichia Pastoris, J. Basis Microbiol., vol. 28, No. 4, 1988, pp. 265–278.

Sakai et al., Cloning and Sequencing of the Alcohol Oxidase–encoding Gene . . . , Gene, vol. 114, 22 Jan. 1992, Amsterdam, pp. 67–73.

Primary Examiner—Nancy T. Vogel
Attorney, Agent, or Firm—Cushman Darby & Cushman IP Group of Pillsbury Madison & Sutro LLP

[57] ABSTRACT

The present invention relates to an expression vector which is induced by methanol and/or glycerol utilizing an alcohol oxidase gene of a methylotrophic yeast; a recombinant methylotrophic yeast containing said vector and capable of accumulating a significantly high amount of an expression product of a heterologous gene; and a method for producing useful products utilizing said recombinant.

The expression vector is constructed by utilizing the promoter and terminator of an alcohol oxidase gene of methylotrophic yeast. Further, a significantly high amount of adenylate kinase, cytochrome C552 or peroxidase is produced by using said expression vector.

9 Claims, 12 Drawing Sheets

Fig. 2A

```
-1667                                                    GAATTCC GGAGTATACG TAAATATATA ATTATATATA ATCATATATA TGAATACAAT GAAAGTAAAT
-1600 ATGATAAGAT TGAAATAATA ACAAACAGCG ATAAATATAT CTCAAAAATGG AGTTACACAA CAAATAATAA TAAAATATAA ATTATAAAAT ATAAAGGAAT
-1500 AAAATAAACC CCACTAATTT ATTTTATTAA AAGATAGATT GGTATCTTTA ATTCTGAAAC TTTATTCACT TTAATTTATT TAACTTATTT
-1400 AATTTATTTT TACCCCAGTT TTTTCAGTCG AGTGCAGCTC CGAAACTTTA TTTGGCTGTG GATTGGCTT GCTGGAATTG
-1300 TCTCCTGCAG GAATTGCTCG GGGTCCGGTT CTCCCGCAGC TGGATATTTG GCTGGCTGCT GCTCTGCCAT CTGCTGTGGC CACCCCCGCA
-1200 TCTCTGGATG CACGCCGTGC AGCTGGACTT GCGTCTACCC TGCAGCCGTG TGCCTCATCT CCCAATCTCT CAATCAGCCA GTCAGCCAGC CAGCCAAAAT
-1100 ACGGGCCAGG CAGGCAGGCA GGCAGGCAGG CAGGCAGCCA CAGGCAGTGA TGCCTTCCCA CGCCCCACCC CGCATAAACA TCCCCAGCAG
-1000 TTTCCCCAGC AGTTTCCCCA GCTTTTCAAT TTAATAAAAT AGCCTGTTTC TGTTTCTGTT TTATATTATA CAATTTTTTA TACTCTTTTG
 -900 GGAATTAAAT AATAATTATA TCATATACCC ATATCACATT TTACTATATT TACTATCTAT AAATAAATTC ATATTATAAT ATTCGCTTAA
 -800 TTAAAATGCT CTTTTCCATC ATCATCATCA TCATCATCAC GAGTTTTCGG TTATCAATAC TCTTTTCATT AACTTCTAGA ATTTCATTAT TTATTTTTA
 -700 TTGACTGGAA ATTTTCAATC AATTTTATT TACTTACATA ATATTCTTAG ATTTAAACTT TTTAGATGAC CGCTATTTTA CTTACTTACT
 -600 TACTTACTTA CTTACTTACT TACTTACATA CCTACTTACT GTGATTTTAT AATATGATAA GAATTAATTT TCATATTTAT GATGATGTAA ATTTAACCTA
 -500 GTATACTATT TTAAAGTTAT CACTATCTTT TAGTGCTGGC ATTTTTTATT CTATTTTCAT ATATGTATAT AAGTAAAATTA AGTATCATCA CGCTGCTTAC
 -400 TGTACGTTTA AAATGTGGAG ATGGAAATAG AGATGGGGAT GAAGATGAAG ATGATGAGAA TTATAAACCA TTCATTCATT AATCAATCAA TATAACTTAT
 -300 AAAAAAATTT ATATTTAAAT ATATTATAAC GAATTAATTT CCTTTATTTT AATAATATCG TTAATTCTTT TAAATTCTAT TTTATTTTAA TTCTTTCTTT ATCATAGTTA
 -200 TCATATATACA ATTATATAAC ATAGATACAC AATTATATTT TTATTATCAT ATTATTTTTT AAAAATATTGA AAAATATTGA TTATTTTAA AATAATATCT TAATTAATTA
 -100 ATTTTTACGA ATATACAAAT TTTAACGACT TTCTTTTTTT AACGAATTTT TAAAAAAACA TAAAAAAACA AAAAAAAAAA AACAAAATTA TTTTTCAATA
```

Fig. 2B

```
         10         20         30         40         50         60         70         80         90        100        110        120
ATGGCTATCCCAGAAGAATTTGACGTTATT GTTTGTGGTGGTGGTTCCACTGGTGTGTT ATTGCAGGTCGTCTTGCAAATGTCGATGAA AATTTAAAAGTTTTATTGATTGAAAATGGT
MetAlaIleProGluGluPheAspValIle ValCysGlyGlyGlySerThrGlyCysVal IleAlaGlyLeuArgLeuAlaAsnValAspGlu AsnLeuLysValLeuLeuIleGluAsnGly 130        140        150        160        170        180        190        200        210        220        230        240
GAAAATAATTAAAATAATCCATGGGTTTAT TTACCAGGTATTTATCCAAGAAATATGAGA TTAGATTCAAAAACTGCAACTTTTTATAAT TCAAGACCATCAAAACATTTAAATGGTCGT
GluAsnAsnLeuAsnAsnProTrpValTyr LeuProGlyIleTyrProArgAsnMetArg LeuAspSerLysThrAlaThrPheTyrAsn SerArgProSerLysHisLeuAsnGlyArg 250        260        270        280        290        300        310        320        330        340        350        360
CGTGCTATTGTTCCTAAGCTAATATCTTA GGTGGTGGTTCATCTATTAATTTTATGATG TATACAAGAGCTTCTGCTTCTGATTATGAT GATTGGGAATCTGAAGGTTGGACTACTGAT
ArgAlaIleValProLysLeuIleSerLeu GlyGlyGlySerSerIleAsnPheMetMet TyrThrArgAlaSerAlaSerAspTyrAsp AspTrpGluSerGluGlyTrpThrThrAsp 370        380        390        400        410        420        430        440        450        460        470        480
GAATTATTACCATTGATGAAAAAATTTGAA ACTTATCAACGTCCTTGTAATAACAGAGAT GTTCATGGTTTTGATGGTCCAATTAAAGTT TCTTTTGGTAATTATACTTATCCTCAATGT
GluLeuLeuProLeuMetLysLysPheGlu ThrTyrGlnArgProCysAsnAsnArgAsp ValHisGlyPheAspGlyProIleLysVal SerPheGlyAsnTyrThrTyrProGlnCys 490        500        510        520        530        540        550        560        570        580        590        600
CAAGATTTCCTTAGAGCTTGTGAAACACAA GGTATCCCATACGTTGATGATTAGAAGAT TTGAAAACTTCTCATGGTGCTGAACAATGG TTAAAATGGATTAACAGAGATTTGGTAGA
GlnAspPheLeuArgAlaCysGluThrGln GlyIleProTyrValAspAspLeuGluAsp LeuLysThrSerHisGlyAlaGluGlnTrp LeuLysTrpIleAsnArgAspPheGlyArg
```

```
       610        620        630
CGTTCTGATATCTGCTCATGCTTTTATTCAT TCAACTATGAGAAATAAGAAATTTATTT
ArgSerAspThrAlaHisAlaPheIleHis  SerThrMetArgAsnLysGluAsnLeuPhe 730        740        750
AGAACCGTTCCATCAAAACCAATTGGTGAT TCTAAAGTTCAAGAACTTTAAAGCTAGA
ArgThrValProSerLysProIleGlyAsp SerLysValSerArgThrPheLysAlaArg 850        860        870
ATTGGTGAACCATCTAAATTAAGAGCTGCT GGTGTTAAACCAATTGTTGAATTACCAGGT
IleGlyGluProSerLysLeuArgAlaAla GlyValLysProIleValGlyLeuProGly 970        980        990
TCTGAATCATTCATGCATTGTCTCTGGT   GATAAGAAGCTCAAAATCAGCTTTTGAT
SerGluSerPheAspAlaPheValSerGly AspLysGluAlaGlnLysSerAlaPheAsp 1090       1100       1110
ATTAGACCAACAGAAGCTGAATTGGCAACT GCTGATAAGGCTTTCCAACAAGGTTGGGAA
IleArgProThrGluAlaGluLeuAlaThr AlaAspLysAlaPheGlnGlnGlyTrpGlu 1210       1220       1230
TTTGGTGATCACTAGATTACCACCAGGA   AAATATGACTATGTCCATTTCTTAGAA
PheGlyAspHisThrArgLeuProProGly LysTyrMetThrMetPheHisPheLeuGlu 1330       1340       1350
TTCGATCCAGGTTTTATGAATGATGACAGA GATATGTGGCCAATGGTTTGGGCATTCAAG
PheAspProGlyPheMetAsnAspAspArg AspMetTrpProMetValTrpAlaPheLys 1450       1460       1470
CCCATTATAAAGTTGATTCCCTGCTAGA   GCTTAGAACAAAGTGCTGAAGATACTAAG
ProHisTyrLysValAspSerProAlaArg AlaLeuGluGlnSerAlaGluAspThrLys 1570       1580       1590
ATTGGTGAAGCTGATAAACATGATCCAAAT CATGTTACTTCTTCTCATATTAACGTTTAC
IleGlyGluAlaAspLysHisAspProAsn HisValThrSerSerHisIleAsnValTyr 1690       1700.      1710
CACGCTGAAACTACATGGCATTGTCTTGGT ACTAACTCCATGGCTCCAAGAGAAGGTAAT
HisAlaGluThrThrTrpHisCysLeuGly ThrAsnSerMetAlaProArgGluGlyAsn 1810       1820       1830
TTAAAGTTGCTGATTATCAGTTGTCCA    GATAATGTTGGTTTGTAATACTTTCTCAACT
LeuLysValAlaAspLeuSerValCysPro AspAsnValGlyLeuCysAsnThrPheSerThr 1930       1940       1950
TCTGAATTAGATATGGAAGTTCCAACAT   AAATTAAAAACTTATGAACAAACTGGTGCT
SerGluLeuAspMetGluValProGlnHis LysLeuLysThrTyrGluGlnThrGlyAla
```

```
2011  TTTTTACTGC TCTTTTTTAA TGATCTCTCT TTATTTTTTT TTCAATCAAT TTATTTATTT AATTTTTTCA CTTTTTATAAT TCTTGATATG ATATGATATG
2111  ATATGATTTT AGTTCTTTGT CTGTTTTTTT TTTTTTTTTT CAAACTTTTC TTTATGAC TTTATACCAA AAATTTCCAA AAATTTCCA AAAAAAAAAC
2211  AATAATGTTC TTTTTACGTC TCTTTCCTTT TACAAAATAT ATTTATTGCC TGCCTCATTT TTTCAAATA CTTTTTTTC CCTGTAACAG TAATTAGTAA
2311  ATTGAAAAAA ATAATTATTA ATTAAGTAA CATTGAGTT TACAATATA GTAATAATAG TCTATCTACA ACCAATATTA AATAATTGA
2421  TCATTAAAA CAACATTAAA AGTACATAAT TAATAAAAGA AAGAGGAGA AACAAAAGCA TAATAAATCA TTAAAATTTG AGTATAG
```

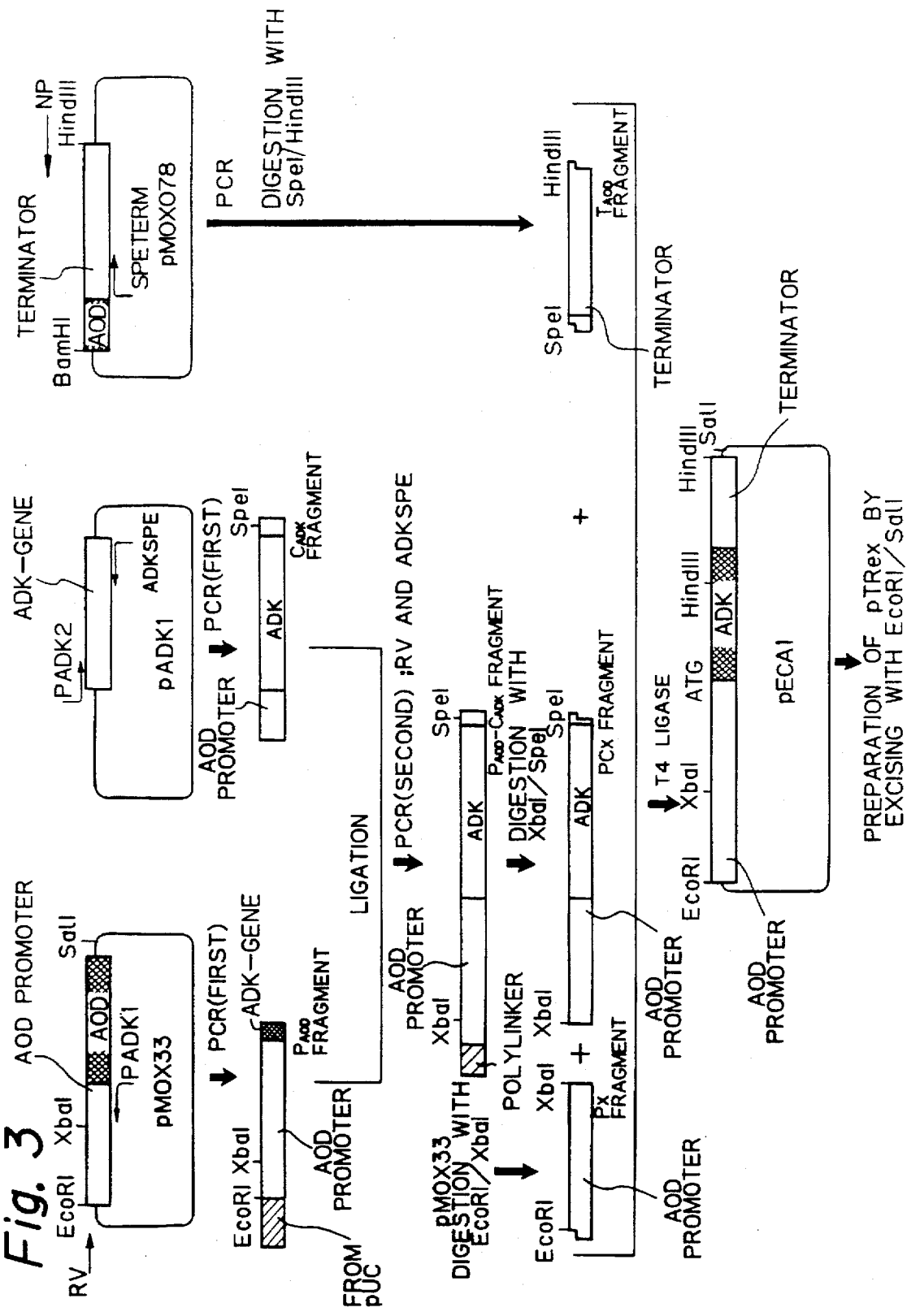

Fig. 7

```
       Hind III
    5' AAGCTTTTTA TCACTAGTGA AATTAGTGAT TATAATGATA TAATCAAAAA TAGTACCTTG GATGAGAAAA GCATTGTGTT TAATATTTAT GTATTGCACT 100
    3' TTCGAAAAAT AGTGATCACT TTAATCACTA ATATTACTAT ATTAGTTTTT ATCATGGAAC CTACTCTTTT CGTAACACAA ATTATAAATA CATAACGTGA ACACTCAATA GGACCGTGCG AGGCAGTCTA AGAGATCCAC AAAATTTATG TAAATGATAT TATCACGTGA TATTAATGAA ACATTTAAT TGTTGTTTTT 200
       TGTGAGTTAT CCTGGCACGC TCCGTCAGAT TCTCTAGGTG TTTTAAATAC ATTACTATA ATAGTGCACT ATAATTACTT TGTAAATTA ACAACAAAAA GCGTCGAGTT ATCAACTGAC TTCTTATGTA CTTTGTGACT ATATAGATTT TGAGTAGTAT TAAGTATTTC TCAGCGCGTA ATAATCAGTG TTGGTCTACC 300
       CGCAGCTCAA TAGTTGACTG AAGAATACAT GAAACACTGA TATATCTAAA ACTCATCATA ATTCATAAAG AGTCGCGCAT TATTAGTCAC AACCAGATGG AGCTAATTAT TACTATATAT TCTCCTATGAT ACGATATTCT GAGAAATGAT TAATAAGCGT TAATATGCAT ACAATAACAA AATGATTAAT ATTAATTAAT 400
       TCGATTAATA ATGATATACT AGAGATACTA TGCTATAAGA CTCTTACTA ATTATTCGCA ATTATACGTA TGTTATTGTT TTACTAAATA TAATTAATTA BglII
       AACAAAGTTA TAAAGTAAAT AAATATAATA AATACAATTG GATAAGTAAG ATAGATCTCT TTTCTATTCG TTATGAACTT ATAACAAACA 500
       TTGTTTCAAT ATTTCATTTA TTTATATTAT TTATGTTAAC CTATTCATTC CTATCTAGAGA AAAGATAAGC AATACTTGAA TATTGTTTGT GTAAGAGTTA AAAGGATATA GATTTATATA TATAAAAGAG TAAACTATAT AGAAGGTAGT GTACTAAATGC TAAGTAAACT AATCCTAAAT AAGTTGAAAA 600
       CATTCTCAAT TTTCCTATAT CTAAATATAT ATATTTTCTC ATTTGATATA TCTTCCATCA CATGATTACG ATTCATTGA TTAGGATTA TTCAACTTT CTAATAAATA CGTTAAATCC AAGTAGTGTA TAGAAATGAA ATAAACAATG TAGAAGTTCA CTAAAGTTCA TAATCTACAT TTATATGTAT TTATAAAAAT 700
       GATTATTTAT GCAATTTAGG CATGTCACAT TTCATCACAT ATTTGTTAC ATCTTTACTT GATTTCAAGT ATTAGATGTA AATATACATA AATATTTTTA TCGCGTGACT TTAACTTAAG ATAGTTATATA GTTAAAACTG CTATAGAAAT AATATGTAAC AATTTATGT TGTATACATT TAATTATATT TAGTTTATAA 800
       AGCGCACTGA AATTGAATTC TATCTAATAT CAATTTGAC GATATCTTTA TTATACATTG TTAAAATACA ACATATGTAA ATTAATATAA ATCAAATATT AAATAAAGTA TATAGTGAAA AAGTGAATAA AATAAAGCTT 3'
       TTTATTTCAT ATATCACTTT TTCACTTATT TTATTTCGAA 5'
                                        Hind III
```

Fig. 9

DELATION MUTANTS

| | PLASMID | EFFICIENCY OF TRANSFORMATION (NUMBER OF COLONY/μgDNA) | |
|---|---|---|---|
| | | C. boidinii | S. cerevisiae |
| 1-850 | pRAC1 | 4.0 × 10² | 1.3 × 10⁵ |
| 243-850 | pRAC12 | <1 | 1.2 × 10⁵ |
| 459-850 | pRAC13 | <1 | 1.1 × 10⁵ |
| 693-850 | pRAC14 | <1 | 1.2 × 10⁵ |
| 1-850 | pRAC1R | 3.2 × 10² | 1.1 × 10⁵ |
| 1-495 | pRAC1R1 | 2.1 × 10² | <1 |
| 1-189 | pRAC1R2 | <1 | <1 |

VECTOR HAVING PROMOTER THAT IS INDUCIBLE BY METHANOL AND/OR GLYCEROL

This is a continuation of application Ser. No. 08/025,416, filed on Mar. 1, 1993, abandoned.

BACKGROUND OF THE INVENTION

1. Field of the Invention

This invention relates to an expression vector comprising the alcohol oxidase gene promoter having the nucleotide sequence represented by Seq. I.D. No. 1, said promoter being inducible by methanol and/or glycerol; a desired heterologous gene linked to the downstream of said promoter; and a terminator having the nucleotide sequence represented by Seq. I.D. No. 2, which termination is located downstream of the heterologous gene. More particularly, the invention relates to a recombinant methylotrophic yeast which contains said vector; and a method for producing useful enzymes, in particular, adenylate kinases, cytochromes C and peroxidases by said recombinant yeast.

2. Prior Art

Since methylotrophic yeasts grow on methanol as a sole carbon source and provide a high cell yield, they have been used to produce raw materials in the chemical industries, for example, aldehydes such as formaldehyde, methyl ketone and formic acid. Further, a number of attempts have been made to utilize cells of these yeasts themselves as protein sources, as well as to utilize intracellular components thereof such as amino acids and vitamins, and some of these attempts have been put into practical use.

In the first step of the methanol metabolic system in methylotrophic yeasts, methanol is oxidized in the presence of oxygen by an alcohol oxidase to produce formaldehyde and hydrogen peroxide. The formaldehyde thus produced is catabolized to generate energy or anabolized to form cellular components. The alcohol oxidase involved in this step is induced by methanol, forms an organelle called peroxisome, together with a catalase which decomposes hydrogen peroxide, and effectively participate in the oxidation of methanol. Therefore, when methylotrophic yeasts are cultured in the presence of methanol, a significantly high amount of an alcohol oxidase is produced and the yield amounts to about 40% of the cellular soluble proteins. Great activity or convenience in culturing have made methylotrophic yeasts a useful source for producing the alcohol oxidase and the catalase. The alcohol oxidase has found its utility as a biochemical reagent to quantitate alcohol or to increase bactericidal effects of ethanol disinfection, while the catalase has been utilized to decompose and eliminate hydrogen peroxide added to food as a bacteriocide.

On the other hand, adenylate kinase is an enzyme which is capable of forming two adenosine diphosphate (ADP) molecules from adenosine monophosphate (AMP) and adenosine triphosphate (ATP) and hence the rate-determining enzyme in the production of ATP in methylotrophic yeasts [Tani, T., p. 253, "Biology of Methylotrophs", Bufferworth Heinemann (1991)]. Adenylate kinase is utilized, for example, in assays for AMP, while ATP is valuable not only as a biochemical reagent but also as an energy source in the synthesis of biochemical compounds with various enzymes. Therefore, if ATP could be produced on a large scale at a low cost from a microbial culture broth or cultured cells, the product could be economically available for various enzymatic reactions which require ATP.

Cytochrome C552 is a hemoprotein which plays an important role in the electron transport system of Hydrogenobacters and is characterized by its heat stability which is superior to cytochromes C of other origins. Recently, various studies and research have been conducted aiming at utilizing cytochrome C as electronic element material. Although it is expected that cytochrome C552 will be ideal as electronic element material due to its heat stability, the prior method for preparing cytochrome C552 using *E. coli* as the host has a problem in that said method provides unsatisfactorily low yields since the cytochrome C552 gene is expressed exclusively under anaerobic conditions.

Peroxidases oxidize various compounds in the presence of hydrogen peroxide and have recently been used, like other oxidases, as clinical diagnostic drugs for quantitating glucose, cholesterol, phospholipids, urea, etc. Also, they are used as labelling enzymes in enzyme linked immunoassays. Particularly, the peroxidase produced and secreted by *Arthromyces ramosus* (ARP) has a significantly higher catalytic activity in the production of chemical emission in systems using chemical emission reagents, which is far superior to other known peroxidases (Japanese Patent Public Disclosure No. 212398/88). However, the drawback with ARP is that the growth rate of the ARP producing bacteria is so slow that costs for producing ARP are high.

As described above, methylotrophic yeasts are especially suitable in the production of valuable substances and enzymes on an industrial scale, since these microorganisms can be easily cultured on a large scale in an inexpensive medium. At present, however, substances that can be produced by methylotrophic yeasts are limited to those which are found in the methanol metabolic system, such as aldehydes, and to those which constitutes methylotrophic yeast, such as amino acids and vitamins. Also the production of enzymes are limited to those found in the methanol oxidation system such as alcohol xidases and catalases.

SUMMARY OF THE INVENTION

The present inventors have conducted extensive studies in order to clarify the expression system of the methanol- and/or a glycerol-inducible alcohol oxidase gene in methylotrophic yeasts and to achieve effective expression of a heterologous gene by taking advantage of said expression system.

Accordingly, it is an object of the present invention to provide an expression vector inducible by methanol and/or glycerol, wherein the promoter and the terminator of the alcohol oxidase gene derived from methylotrophic yeasts are utilized; and a recombinant methylotrophic yeast which contains said expression vector and produces a significantly high amount of an expression product from the heterologous gene.

It is another object of the present invention to provide a method for preparing an expression product of a heterologous gene, which method utilizes the expression vector of the present invention and produces a significantly high amount of the target product in a methylotrophic yeasts. The term "heterologous gene" as used herein means any gene other than the alcohol oxidase gene derived from methylotrophic yeasts.

BRIEF DESCRIPTION OF THE DRAWINGS

FIGS. 2A, 2B, 2C and 2D the nucleotide sequence of a DNA fragment which contains the alcohol oxidase gene (SEQ ID NO. 1, SEQ ID NO. 2 and SEQ ID NO. 3) and the amino acid sequence (SEQ ID NO:5) which was deduced from said nucleotide sequence, wherein the underlined portions represent the TATA sequence, the transcription termination signal and the poly A addition signal, respectively. The underlined portion in the amino acid sequence represents the portion which agree with the N-terminal sequence determined for the purified enzyme.

FIG. 3 shows a process for preparing an adenylate kinase expression cassette which comprises the promoter and the terminator of the alcohol oxidase gene.

FIG. 7 shows the nucleotide sequence of an autonomously replicating sequence (ARS) from the chromosomal DNA of *Candida boidinii* (SEQ ID NO. 4).

FIG. 9 shows efficiency of transformation by deletion plasmids using *Candida boidinii* and *Saccharomyces cerevisiae* as host cells.

DETAILED DESCRIPTION OF THE INVENTION

Figure 1:
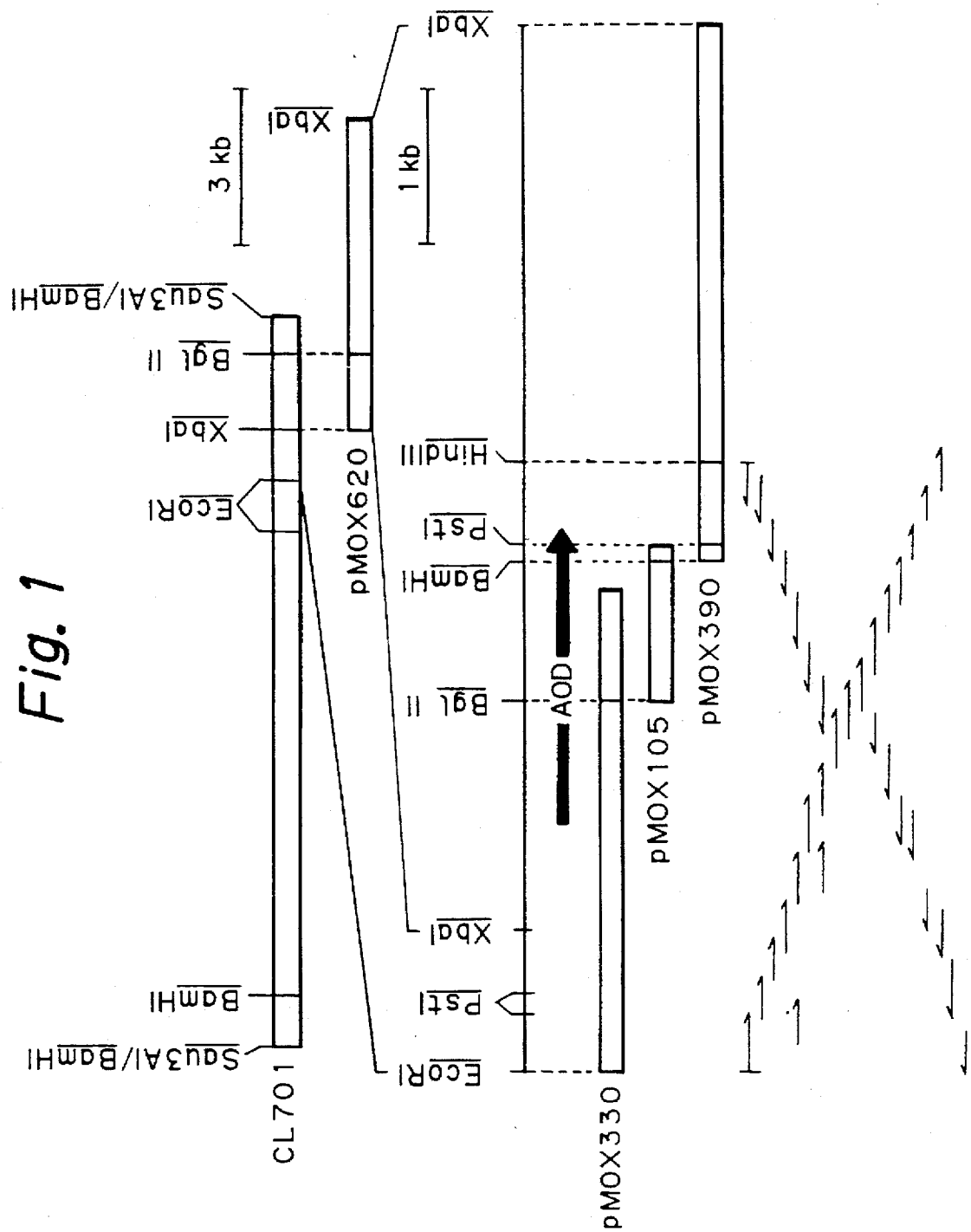
FIG. 1 shows restriction enzyme maps of the plasmids which taken together contain the alcohol oxidase gene used in the present invention and a process for preparing said plasmids.

In order to achieve the above-mentioned objects, the present inventors have clarified the nucleotide sequence of the alcohol oxidase gene carried by a strain of methylotrophic yeasts, *Candida boidinii*, as well as the nucleotide sequence of the promoter and the terminator related to said gene, and have constructed an expression cassette which utilizes these elements. Further, the present inventors have confirmed, by the successful production of a significantly high amount of a adenylate kinase, a cytochrome C and a peroxidase, that expression of a heterologous gene product could be achieved at a much higher efficiency when the gene was in said expression cassette than in the natural expression system of said heterologous gene. The present invention was accomplished on the basis of these findings.

The expression vector of the present invention contains, in the expression cassette, the promoter and the terminator regions of the alcohol oxidase (hereinafter referred to as AOD) gene derived from a methylotrophic yeast. However, the AOD encoding region has been replaced with a heterologous gene. Said promoter and terminator were discovered by the present inventors and have nucleotide sequences represented by Seq. I.D. No. 1 and Seq. I.D. No. 2, respectively.

The alcohol oxidase gene and the elements of the expression system thereof to be used in the present invention can be obtained by screening a gene library of methylotrophic yeast chromosomal DNA by colony hybridization or plaque hybridization. As the probe, an appropriate synthetic oligonucleotide corresponding to the N-terminal amino acid sequence of alcohol oxidase purified from a methylotrophic yeast can be used. The preparation of the gene library, the colony hybridization and the plaque hybridization can be performed in accordance with conventional methods. The nucleotide sequence of the alcohol oxidase gene thus obtained can be determined by a conventional method and then the non-coding regions which are located at the 5'-end and 3'-end thereof can be used as the promoter and the terminator, respectively. Then, a desired heterologous gene can be inserted between the promoter and the terminator again by a conventional method so that an expression cassette is completed.

The expression vector of the present invention can be constructed by inserting the above-mentioned expression cassette which contains a desired heterologous gene into an appropriate vector. As examples of such a vector, known *Escherichia coli* vectors such as pUC18, pUC19 and pBR322 may be mentioned. The insertion of the heterologous gene, the AOD promoter and the AOD terminator into these vectors can be effected by those skilled in the art either in accordance with the description in the Examples given hereinafter or any of the conventional techniques.

The present invention further relates to cells which have been transformed with the above-mentioned expression vector, as well as a method comprising culturing said transformed cells and isolating and purifying a peptide or a protein which is the expression product of the desired heterologous gene.

When the transformed cells of the present invention are cultured in the presence of methanol and/or glycerol, expression of the heterologous gene is induced so that a significantly high amount of the desired peptide or protein will be produced inside or outside the cells.

In one embodiment of the present invention, when a host cell is transformed with the expression vector of the present invention, the heterologous gene in said cassette can be integrated into the chromosomal DNA of the host cells by a so-called homologous recombination and the expression cassette will be carried stably in the host. In this embodiment, hosts are not limited to any specific ones, but preferred host cells for effecting the transformation are yeasts, most preferably, the same methylotrophic yeast from which the AOD gene expression system was obtained or methylotrophic yeasts close thereto and *Saccharomyces cerevisiae*. However, there may be a great number of other hosts which are compatible with the vector of the present invention and capable of allowing expression of the heterologous gene in the vector.

In order to integrate the expression cassette in the vector into chromosomal DNA of the host cells, an appropriate selection marker gene may be used wherein said marker gene has a sequence homologous to the gene on chromosomal DNA of the specific host cell. Selection markers for such a purpose can be easily selected by a skilled person. As an example, a preferred marker is a certain gene which exists on a chromosome and relates to the metabolism of the host cells. Namely, it is preferred to use a host which has been modified in such a manner that the above-mentioned gene on the chromosome will be inactivated by an appropriate means such as a mutation. The host can then be subjected to a homologous recombination with an expression vector containing the corresponding intact gene, whereupon only transformants which contain the normal metabolism gene can grow to be selected. Therefore, if such a marker gene has been introduced to the expression vector, a homologous recombination will take place between the marker gene in said expression vector and the corresponding portion of the chromosomal DNA, whereby the expression cassette of the heterologous gene will simultaneously be integrated into the chromosomal DNA. Transformants can be screened by the induction of the expression of the integrated heterologous gene in the presence of methanol or glycerol and by the subsequent production of the desired peptide, etc.

In another embodiment of the present invention, the expression vector of the present invention is capable of replicating as a plasmid in host cells, wherein said expression vector comprises a DNA fragment of an autonomously replicating sequence (ARS) of a methylotrophic yeast which is inserted into said vector in place of or in addition to said marker gene. As examples of such vectors, known *Escherichia coli* vectors such as pUC18, PUC19 and pBR322 may be mentioned. Although preferred host cells are the same cells as described above, most preferably, methylotrophic yeasts from which the AOD expression system was obtained, other methanophil bacterium, or *Saccharomyces cerevisiae* can be used.

The transformation of the host cells such as methylotrophic yeasts and the recovery of the transformed cells which have an expression cassette integrated in their chromosomal DNA can be carried out by using a known method [Sakai, Y. et al., J. Bacteriol., 173, 7458–7463 (1991)]. As an adenylate kinase gene, the one derived from *Saccharomyces cerevisiae* has already been disclosed [Konrad, M., J. Biol. Chem., 263, 19468–19474 (1988)]. Also, examples of such an autonomously replicating sequence and integration thereof into a vector are disclosed in Kurts, M. B. et al., Mol. Cel. Biol., 7, 209–217 (1987). Further, any known method can be used to isolate and purify the peptide or protein produced in the cell culture of the transformed methylotrophic yeast.

The cytochrome C552 gene derived from *Hydrogenobacter thermophilus* is disclosed by Sanbongi et al. [Sanbongi, Y., Yang, J. H., Igarashi, Y. and Kodama, T., Eur. J. Biochem., 198, 7–12 (1991)].

The peroxidase gene derived from *Arthromyces ramosus* (ARP) is disclosed in EP 0486067.

The expression vector having the alcohol oxidase expression cassette in accordance with the present invention and a transformant containing said vector are remarkably advantageous as follows:

i) The strong promoter, which is inducible by methanol and/or glycerol contained therein, results in a remarkably high expression efficiency.

ii) Addition of chemicals such as an antibiotic to the medium which is otherwise needed to stabilize the heterologous gene can be dispensed with, since the heterologous gene has been integrated into the chromosomal DNA of the host cell so as to be retained stably over a prolonged culture period.

iii) Since the expression vector of the present invention can be induced by simply adding methanol and/or glycerol to the medium, the conditions for the induction can be easily established, and the inducer substance (methanol and/or glycerol) is inexpensive.

The following Examples will be given to further illustrate the present invention. However, it is to be understood that the present invention is not limited thereto.

Although the present invention will be described below by using the promoter and the terminator of the alcohol oxidase gene in the expression cassette and URA3 gene as the marker gene, it is apparent that the elements employable in the present invention are not limited thereto. Thus, other marker genes can also be employed. Also, although the adenylate kinase gene, the cytochrome C gene, the peroxidase gene and a G418 resistant gene are used as specific examples, the heterologous gene of the present invention is not limited thereto.

EXAMPLE 1

In this Example, the alcohol oxidase gene was obtained from *Candida boidinii* S2 AOU-1 strain [Tani, Y. et al., Agric. Biol. Chem., 49, 2699–2706 (1985)] and the nucleotide sequence thereof was determined. This strain was designated as *Candida boidinii* SAM 1958 and deposited at the Fermentation Research Institute of the Agency of Industrial Science and Technology under the accession number FERM BP3766 on Feb. 25, 1992.

(1) Preparation of libraries

Phage library

Chromosomal DNA was isolated from cells of *Candida boidinii* S2 AOU-1 strain. The isolation of the DNA could be carried out by, for example, the method of Cryer et al. [Cryer, D. R. et al., Meth. Cell. Biol., 12, 39–44 (1975)]. After the isolation, the DNA was partially digested with the restriction enzyme Sau3AI, the digest was electrophoresed on a 0.5% agarose gel, and DNA fragments of 12 to 22 kb were recovered from the gel. These DNA fragments were ligated with EMBL3 arm [purchased from Stratagene; Frischauf, A., et al., J. Mol. Biol., 170, 827–842 (1983)]. The armed fragments were introduced into the in vitro packaging system of λ phage, Giga Pack Gold (purchased from Stratagene). As a result of the evaluation which employed *E. coli* P2392 strain as the host, $1.1 \times 10^5$ recombinant phages, which constituted a phage library, were obtained.

Plasmid library

On the other hand, another aliquote of the Candida DNA isolated as above by the method of Cryer et al. was digested completely with the restriction enzyme XbaI and the digest was electrophoresed on a 0.7% agarose gel. DNA fragments of 4 to 7 kb were recovered from the gel. The DNA fragments thus recovered were inserted into the XbaI site of the vector pBluescript II KS$^+$ (purchased from Stratagene). An *E. coli* XL1-Blue strain was then transformed with said vector to give a plasmid library.

(2) Screening of libraries

The N-terminal amino acid sequence of *Candida boidinii* alcohol oxidase was determined to be Ala-Ile-Pro-Glu-Glu-Phe-Asp-Val-Ile-Val-(SEQ ID NO. 6)-Ile-Val- by a Gas Phase Peptide Sequencer (Model 120-A, Applied Biosystems). Then, the following three synthetic nucleotide probes which correspond to said N-terminal amino acid sequence were synthesized: probe 1: 5'-TCRAGDGGRATNGCCAT-3' (SEQ ID NO. 7), probe 2: 5'-ACRATRACRTCRAAYTC-3' (SEQ ID NO. 8), and probe 3: 5'-ACRTCRAAYTCRAGDGG-3' (SEQ ID NO. 9), wherein R represents A or G, Y represents C or T, H represents A, C or T, D represents A, G or T and N represents any of G, A, T and C. Using these synthetic nucleotides as probes, the gene libraries prepared in the above Example 1-(1) were screened by plaque hybridization or colony hybridization. The hybridization was carried out at 37° C. for 14 hours in accordance with the known method [Sambrook, J., et al., "Molecular Cloning", A Laboratory Manual, 2nd edn. (1989)]. Then, the filter was washed three times in 6×SSC-0.1% SDS at 37° C. and dried. Then, positive clones were detected by autoradiography. As a result, a positive clone, CL701, was selected from the phage library, while a clone which contained plasmid pMOX620 was selected from the plasmid library as a positive clone.

(3) Subcloning

Restriction enzyme maps of CL701 and pMOX620 were prepared and compared with each other. It turned out that these clones had a XbaI-Sau3AI DNA fragment (2.3 kb) in common, as shown in FIG. 1. Referring to this figure, the EcoRI-SalI DNA fragment (3.3 kb, the SalI site exists in the vector EMBL3) of CL701, and the BglII-PstI DNA fragment (1.05 kb) and the BamHI-XbaI DNA fragment (3.9 kb) of pMOX620 were inserted into pBluescript II KS⁺ or KS⁻ and pMOX330, pMOX105 and plasmid pMOX390 were constructed, respectively.

(4) Determination of nucleotide sequence

The nucleotide sequences of the inserted DNA fragments in plasmids pMOX330, pMOX105 and pMOX390 constructed in the above Example 1-(3) were determined in accordance with the strategy shown by the arrows in FIG. 1. The inserted fragments from these plasmids were cloned into phage M13 in both directions and the fragments were made double stranded. These double stranded DNAs (RF) were subjected to digestion with $E.\ coli$ exonuclease III to prepare double stranded DNAs having deletions of various lengths from their end. The method for preparing plasmids having such deletions by exonuclease III is described in detail in "Zoku Seikagaku Jikken Koza, vol. 1, Idenshi Kenkyu-ho II" pages 289-305. Subsequently, $E.\ coli$ JM109 was transformed with these double stranded DNAs having various deletions to propagate the phage clones having the various deletions. The degrees of the deletions in the double stranded DNAs prepared from the phage clones were examined on the basis of the cleavage patterns with restriction enzymes. Then, single stranded phage DNAs were prepared from appropriate clones. By using these single stranded phage DNAs as templates, the nucleotide sequences were determined by the dideoxy method [Sanger, F. et al., Proc. Natl. Acad. Sci. U.S.A., 74, 5463 (1977)]. The nucleotide sequence of the inserted DNA fragment in each of plasmids pMOX330, pMOX105 and pMOX390 was determined by linking the nucleotide sequences of the clones to each other. The nucleotide sequences of these plasmids were further linked together to give the total nucleotide sequence (4.2 kb) ranging from the EcoRI site to the HindIII site in FIG. 1. The resulting sequence is shown in FIGS. 2A, 2B, 2C and 2D (SEQ ID NO. 1, 2 and 3).

In FIGS. 2A, 2B, 2C and 2D, there is an open reading frame consisting of 1989 base pairs ranging from ATG (base No. 1–No. 3) to TAA (base No. 1990–No. 1992). From the following observation, it was clarified that this open reading frame encoded the target alcohol oxidase gene.

i) The amino acid sequence deduced from the nucleotide sequence showed 77% and 73% homologies to the amino acid sequences of the alcohol oxidases of methylotrophic yeasts *Hansenula polymorpha* [Ledeboer, A. M. et al., Nucleic Acids Res., 13, 3063–3082 (1985)] and *Pichia pastoris* [Koutz, P. et al., Yeast, 5, 167–177 (1989)], respectively.

ii) The N-terminal amino acid sequence which was deduced from the nucleotide sequence was identical with the N-terminal amino acid sequence of the purified enzyme [underlined under the amino acid sequence in FIGS. 2A, 2B, 2C and 2D].

iii) The amino acid composition deduced from the nucleotide sequence was identical with that of the purified enzyme.

iv) The molecular weight (72–75 kDa) of the enzyme as determined by SDS-polyacrylamide gel electrophoresis agreed with the value (73,947) calculated from the deduced amino acid composition.

Upstream from the 5'-end of the coding region, a TATA sequence which is required for transcription in eukaryotic cells was observed, while a transcription termination signal and a poly A addition signal were observed downstream from the 3'-end of the coding region [each underlined under the nucleotide sequence in FIGS. 2A, 2B, 2C and 2D]. The nucleotide sequences upstream from the 5'-end (i.e., promoter region) (SEQ ID NO. 1) and downstream from the 3'-end (i.e., terminator region) (SEQ ID NO:2) showed no significant homologies to those of the above-mentioned *H. polymorpha* and *P. pastoris*.

EXAMPLE 2

This example shows the construction of an expression vector which comprises as the heterologous gene an adenylate kinase gene from a yeast (*Saccharomyces cerevisiae*) and further comprises the promoter and the terminator portions of the alcohol oxidase gene, obtained in the above Example 1, from *Candida boidinii* S2 AOU-1. The example further shows the transformation of a strain of *Candida boidinii* with said expression vector.

(1) Preparation of expression cassette

An expression cassette containing an adenylate kinase gene between the promoter and the terminator of the alcohol oxidase (AOD) was constructed [FIG. 3]. The method for obtaining the adenylate kinase (ADK) gene and determining the nucleotide sequence thereof is disclosed by Konrad [Konrad, M., J. Biol. Chem., 263, 19468–19474 (1988)].

In order to prepare the promoter and the terminator regions of the alcohol oxidase gene as well as the structural gene of adenylate kinase, polymerase chain reactions (PCR) were used. As primers for the PCRs, the following four oligonucleotides were synthesized.

PADK1 (37 mer): 5'-GGATTCTGAACTAGA CATTATTGAAAAATAATTTTGT-3' (SEQ ID NO:10)
PADK2 (37 mer): 5'-ACAAAATTATTTTT CAATAATGTCTAGTTCAGAATCC-3' (SEQ ID NO:11)
SPETERM (29 mer): 5'-GGAACTAGTTAA TTCAACAAGTTGTATCT-3' (SEQ ID NO:12)
ADKSPE (31 mer): 5'-GGAACTAGTTCA TTAATCCTTACCTAACTTG-3' (SEQ ID NO:13)

The normal primer (NP: 17 mer) and the reverse primer (RV: 17 mer) were homologous to the nucleotide sequences downstream from the 3'-end and upstream from the 5'-end of the multicloning site, respectively. These primers were purchased from Takara Shuzo Co., Ltd. The primers PADK1 and PADK2, which are complementary to each other, were used to bind AOD promoter and ADK gene. The underlined portions of PADK1 and PADK2 were complementary to the nucleotide sequences of the 3'-end of AOD promoter and downstream from the 3'-end of the initiation codon of ADK gene, respectively. The primer SPETERM contained the nucleotide sequence (underlined portion) which was identical to the 5'-end of the AOD terminator and carried a SpeI site (ACTAGT) at the positions 4 to 9 from the 5'-end. The primer ADKSPE contained the nucleotide sequence (underlined portion) which was complementary to downstream from the 3'-end of the ADK gene and carried a SpeI site (ACTAGT) at the positions 4 to 9 from the 5'-end.

First PCR

The plasmid, pMOX330 [FIG. 1], which contained AOD promoter was mixed with the primers RV and PADK1, and a PCR was conducted. The reaction product thus obtained was electrophoresed on an agarose gel and the amplified DNA fragment was recovered. The recovered DNA fragment ($P_{AOD}$ fragment) comprised a multicloning site (with the 5'-end flanking sequence thereof) which was located to the 5'-end of the AOD promoter, and further a primer PADK1 sequence located to the 3'-end of the AOD promoter.

On the other hand, the plasmid, pADK1, which contained the structural gene of ADK [Konrad, M., J. Biol. Chem., 263, 19468–19474 (1988)], was mixed with the primers PADK2 and ADKSPE, and a PCR was conducted. After the reaction the product thus obtained was fractionated by electrophresis on an agarose gel, and the amplified DNA fragment ($C_{ADK}$ fragment) was recovered. The recovered CADK fragment comprised a sequence of the primer PADK2 located upstream from the 5'-end of the ADK gene and a SpeI site to the 3'-end of the ADK gene.

Second PCR

The fragments $P_{AOD}$ and $C_{ADK}$ obtained from each of the first PCRs were mixed, the primers RV and ADKSPE were added thereto, and the mixture was subjected to a second PCR, whereupon the DNA fragment thus amplified comprised a linkage between $P_{AOD}$ fragment and $C_{ADK}$ fragment ($P_{AOD}$-$C_{ADK}$ fragment). The successful amplification of $P_{AOD}$-$C_{ADK}$ fragment could be achieved because the nucleotide sequence at the 3'-end of $P_{AOD}$ fragment was complementary to that at the 5'-end of $C_{ADK}$ fragment (refer to the nucleotide sequences of primers PADK1 and PADK2) so that a double strand was formed in this portion and, as a result, $P_{AOD}$-$C_{ADK}$ fragment was formed by the PCR reaction. Another reason for the success was that the primers, RV and ADKSPE, annealed during the reaction to each end of the $P_{AOD}$-$C_{ADK}$ fragment, which enabled the amplification of the $P_{AOD}$-$C_{ADK}$ fragment in the PCR reaction. The amplified $P_{AOD}$-$C_{ADK}$ fragment was cleaved with XbaI/SpeI and the products were electrophoresed on an agarose gel to recover a fragment referred to as $PC_x$ in FIG. 3. The $PC_x$ fragment comprised the portion of the AOD promoter downstream from the 3'-end of the XbaI site, together with the ADK region. On the other hand, pMOX33 (FIG. 1) was cleaved with EcoRI/XbaI to recover a fragment referred to as $P_x$ in FIG. 3. The $P_x$ fragment comprised the portion of AOD promoter upstream from the 5'-end of the XbaI site.

Third PCR

A DNA fragment of 0.6 kb, obtained by cleaving plasmid pMOX390 with BamHI/HindIII, was then inserted into the BamHI/HindIII site of pBluescript II KS$^+$ to construct the plasmid pMOX078. Plasmid pMOX078 contained the terminator region of AOD gene. Primers, SPETERM and NP, were added to plasmid pMOX078, followed by a PCR. The product was cleaved with SpeI/HindIII and fractionated by agarose gel electrophoresis in order to recover the amplified DNA fragment ($T_{AOD}$ fragment). The $T_{AOD}$ fragment had SpeI and HindIII sticky ends at the 5'- and 3'-ends of the AOD terminator, respectively.

Construction of the Cassette

The three DNA fragments thus obtained ($P_x$, $PC_x$ and $T_{AOD}$ fragments) and the DNA fragment obtained by the cleavage of the vector pBluescript II KS$^+$ with EcoRI/HindIII were ligated together using T4 ligase to construct the plasmid pECA1. Plasmid pECA1 contained the expression cassette consisting of the portion of AOD promoter downstream from the 3'-end of the EcoRI site, the ADK structural gene and the portion of AOD terminator upstream from the 5'-end of the HindIII.

(2) Construction of expression vector

Figure 4:
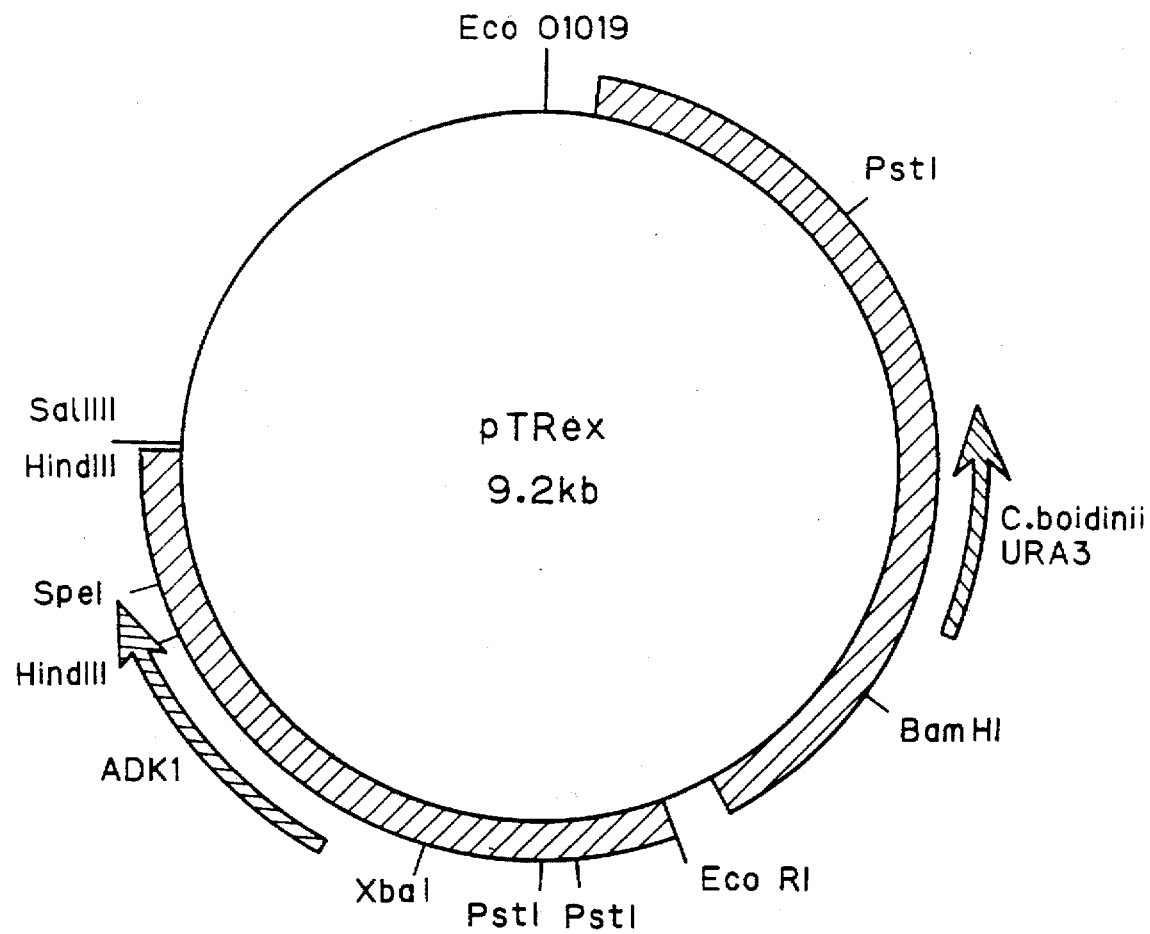
FIG. 4 shows a restriction enzyme map of the alcohol oxidase expression vector pTRex wherein the thick lines represent DNA fragments which contain ADK gene and URA3 gene, respectively.

From plasmid pRCU350 which contained URA3 gene of *Candida boidinii*, the URA3 fragment was excised with SalI and the fragment was blunt-ended with T4 DNA polymerase. Then the fragment was inserted into the NdeI site of plasmid pUC19 to prepare the plasmid pCU350. The methods for obtaining URA3 gene of *Candida boidinii* and preparing plasmid pRCU350 are disclosed by Sakai et al. [Sakai, Y. et al., J. Bacteriol., 173, 7458–7463 (1991)]. The expression cassette was excised from plasmid pECA1 with EcoRI/SalI and inserted into the EcoRI-SalI site of plasmid pCU350 to prepare an expression vector, which was designated as pTRex. FIG. 4 shows the restriction enzyme map of the vector pTRex. The vector comprised the ADK expression cassette of the ADK gene and the URA3 gene which were inserted into the SalI site and the NdeI site of plasmid pUC19, respectively.

(3) Transformation

A uracil-requiring strain (TK62 strain) was obtained from *Candida boidinii* S2 AOU-1 strain. The method for obtaining said uracil-requiring strain and the fact that this uracil-requiring strain has a mutation in the URA3 gene are disclosed by Sakai et al. [Sakai, Y. et al., J. Bacteriol., 173, 7458–7463 (1991)].

Said uracil-requiring strain was transformed with pTRex to obtain a transformant of *Candida boidinii* which was capable of producing a significantly high amount of the adenylate kinase. The transformation was carried out by the lithium method [refer to Ito, H. et al., J. Bacteriol., 153, 163–168 (1983)] or the spheroplast method [Hinnen, A. et al., Proc. Natl. Acad. Sci. U.S.A., 75, 1929–1933 (1978)]. Screening of transformants is disclosed in detail by Sakai et al. [Sakai, Y. et al., J. Bacteriol., 173, 7458–7463 (1991)]. In this transformant, the URA3 gene from plasmid pRTex underwent a homologous recombination with the URA gene in the *Candida boidinii* chromosomal DNA so that the ADK expression cassette was integrated into the chromosomal DNA. Accordingly, when this recombinant was cultured in a medium containing methanol, it exhibited stable production of the adenylate kinase as will be described in Example 3.

EXAMPLE 3

This Example describes a production of the adenylate kinase by utilizing a transformed *Candida boidinii* having the expression cassette of the adenylate kinase gene integrated in the chromosomal DNA.

Figure 5:
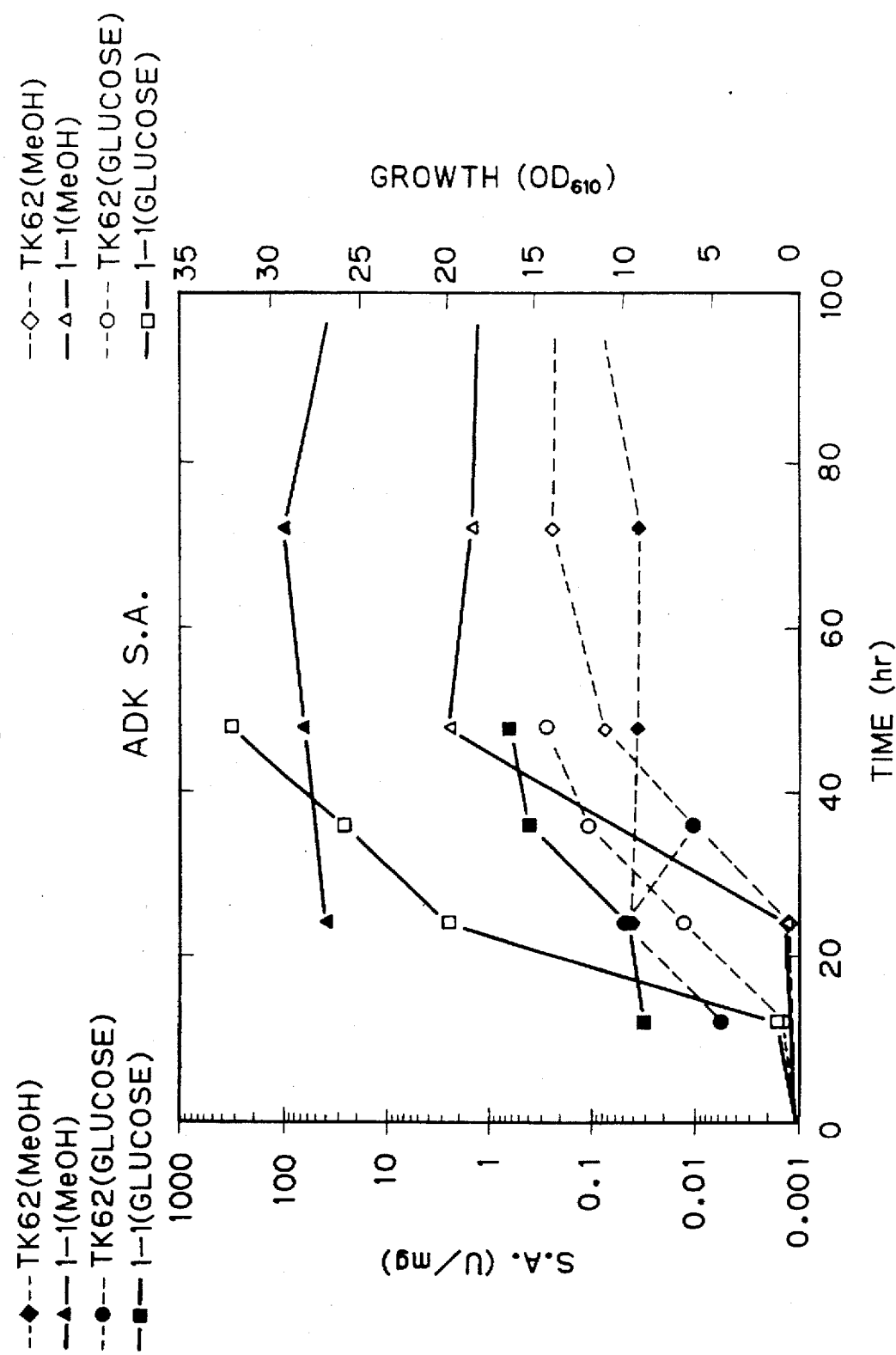
FIG. 5 shows adenylate kinase level and the cell growth with respect to 1-1 strain, which expresses adenylate kinase, and the parent strain (TK62 strain) thereof when they were grown in a methanol or a glucose medium, wherein the open marks represent the cell growth as determined by OD610 and ◇ shows the data for TK62 strain in the methanol medium, △ shows the data for 1-1 strain in the methanol medium, o shows the data for TK62 strain in the glucose medium and ☐ shows the data for 1-1 strain in the glucose medium; whereas the corresponding solid marks represent the adenylate kinase activity of the corresponding strain in the corresponding medium.

A transformant (1-1 strain) and its parent strain (TK62 strain) were cultured side by side in a medium containing methanol or glucose as the major carbon source, while monitoring the cell number and intracellular adenylate kinase activities over the course of time (FIG. 5). The medium for methylotrophic yeasts is disclosed by Sakai et al. [Sakai, Y., et al., Appl. Environ. Microbiol., 53, 1812–1818 (1987)]. Methanol or glucose was added at 2%. The method for determining the adenylate kinase activities is disclosed by Brolin et al. [Brolin, S. E., et al., Methods of Enzymatic Analysis, vol. 3, Third Edition, 540–544 (1983)], wherein 1 unit of the enzyme is defined as the enzymatic activity required to yield 2 µmole of ADP at 24° C. in 1 minute. After culturing in the methanol medium for 72 hours, 1-1 strain showed 93.5 U of adenylate kinase activity per mg of cell protein. Compared with the adenylate kinase activity of the parent strain (0.0328 U), the enzymatic activity of the transformant was greater by 2900 times. This increase of the enzymatic activity was never observed in the glucose medium, indicating that the expression of the adenylate kinase was induced by methanol.

According to the present invention, the alcohol oxidase gene of methylotrophic yeast *Candida boidinii* was obtained and an expression vector of methylotrophic yeast was prepared by using the promoter and terminator of said gene. Further, by culturing a methylotrophic yeast transformed with said expression vector in a liquid medium, an adenylate kinase could be produced in a high amount by addition of methanol. This easy method for obtaining adenyl kinase will enable production of ATP by using the enzyme on an industrial scale.

EXAMPLE 4

Expression induced by various carbon sources

This example shows that the expression vector comprising the promoter and the terminator regions of the alcohol oxidase gene from *Candida boidinii* enables expression of an adenylate kinase, and that said expression is induced by glycerol as well as methanol, but not by ethanol or glucose. Further, this example shows that said expression vector functions also in *Saccharomyces cerevisiae* as confirmed by the expression of G418 resistant gene which was strongly induced by addition of glycerol.

Table 1 shows adenylate kinase activities after culturing the transformant 1-1 strain, prepared in Example 3, for 24 hours in the presence of glucose, ethanol, methanol, glycerol or mixtures thereof. Methanol and glycerol activated AOD promoter and increased the expression of the adenylate kinase. By the combination of methanol and glycerol, the transformant showed the highest expression, which corresponded to 1.7 times relative to induction by methanol alone. The induction by methanol and glycerol was completely suppressed with glucose and ethanol. Since methanol and glycerol are inexpensive carbon sources, heterologous gene products can be produced industrially at a low cost by the transformant of the present invention. In addition, unlike methanol, glycerol can be added to the medium at a high concentration without causing any adverse effects to the growth of the transformants in order to increase the final cell concentration. Therefore, glycerol is the most preferred carbon source for producing peptides or proteins by said methanol yeasts.

TABLE 1

Effect of Carbon Sources on ADK Activity of 1—1 strain

| Carbon source | Specific Activity (U/mg) |
|---|---|
| Glucose (2%, w/v) + Methanol (1.5%, v/v) | 0.77 |
| Glucose (2%, w/v) | 0.40 |
| Ethanol (1.5%, v/v) + Methanol (1.5%, v/v) | 0.25 |
| Ethanol (1.5%, v/v) | 0.08 |
| Glycerol (3%, v/v) + Methanol (1.5%, v/v) | 223 |
| Glycerol (3%, v/v) | 17.3 |
| Methanol (1.5%, v/v) | 135 |

An expression cassette containing G418 resistant gene between the promoter and the terminator of the alcohol oxidase (AOD) gene was constructed. G418 resistant gene from Transposon Tn5 was obtained from plasmid PNEO (Pharmacia). The construction of the expression cassette was carried out by polymerase chain reactions (PCR) in a manner similar to that disclosed in Example 2. The expression cassette thus constructed was inserted into YIp vector pRS406 (Stratagene) containing the URA3 gene from *Saccharomyces cerevisiae*. Transformants that contained said expression cassette integrated as a result of the homologous recombination into the URA3 gene portion of the uracil requiring yeast host (*Saccharomyces cerevisiae*, YPH500 strain; Sikorski, R. et al., Genetics, 122, 19–27, 1989), were screened on the basis of uracil-independency. Resistance of the transformed yeasts against G418 was examined on the basis of the growth in a medium containing various concentrations (0–100 mg/ml) of G418. The transformed yeasts were able to grow even in the presence of 100 mg/ml of G418 in a medium containing 3% glycerol, while the non-transformed host yeast could not grow in a medium containing more than 0.1 mg/ml of G418. When cultured with 2% glycerol as a sole carbon source, said transformants were not able to grow in a medium containing more than 0.1 mg/ml of G418, just like the non-transformed host yeast. These results indicated that the expression cassette utilizing the promoter and the terminator of the alcohol oxidase (AOD) gene derived from the methylotrophic yeast functioned satisfactorily in *Saccharomyces cerevisiae*, and was strongly induced by the addition of glycerol to the medium.

EXAMPLE 5

Figure 6:
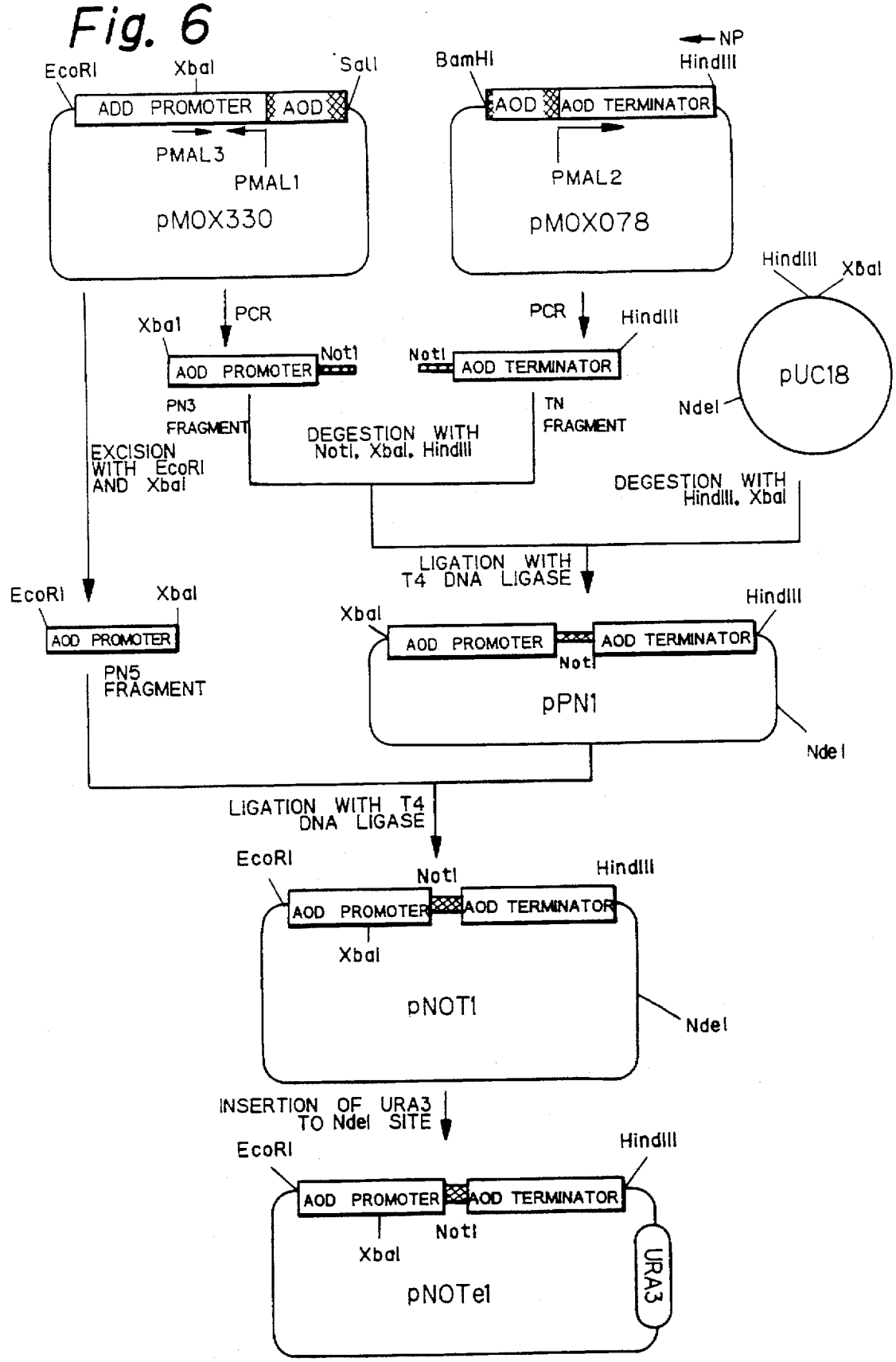
FIG. 6 shows a process for preparing the plasmid which contains the promoter and the terminator of the alcohol oxidase gene and a NotI site between them.
Figure 8A:
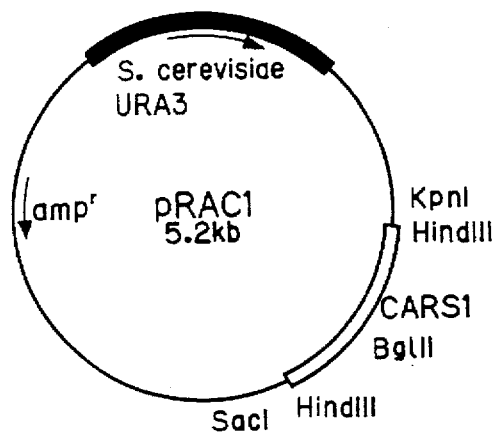
FIGS. 8A, 8B, 8C and 8D show restriction enzyme maps of the four plasmids, pRAC1, pRAC2, pBARCU1 and pBARCU2.
Figure 8B:
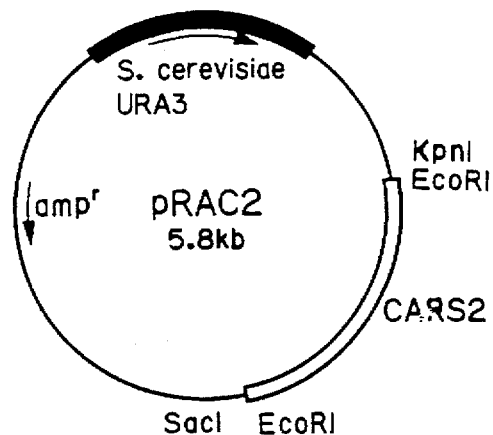
Figure 8C:
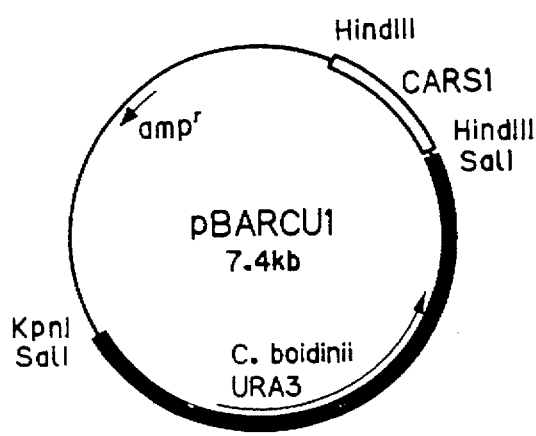
Figure 8D:
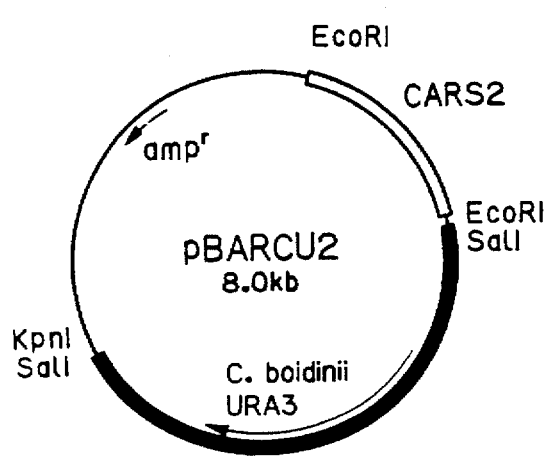

In addition to the expression vector constructed in Example 2, another expression vector was prepared. Thus, the promoter and the terminator regions of the alcohol oxidase gene from *Candida boidinii* S2AOU-1 which was obtained in Example 1 were used, and the nucleotide sequence of NotI site was inserted between said promoter and said terminator (FIG. 6). Cytochrome C552 gene derived from *Hydrogenobacter thermophilus* was inserted into said expression vector in an attempt to produce cytochrome C552 by transforming *Candida boidinii* with said vector.

(1) Isolation of AOD promoter/terminator

A multiple-purpose expression cassette was prepared, wherein said vector comprised a nucleotide sequence of NotI site inserted between the promoter and the terminator of the alcohol oxidase (AOD) gene.

In order to excise the alcohol oxidase gene and the promoter and the terminator regions of the alcohol oxidase gene, polymerase chain reactions (PCR) were used. As primers for the PCRs, the following three oligonucleotides were synthesized.

PMAL1 (29mer):
5'-GGGCGGCCGCTATTGAAAAATAATTTTGT-3'
(SEQ ID NO.14)

PMAL2 (30mer):
5'-GGGCGGCCGCTAATTCAACAAAGTTGTATCT-3'
(SEQ ID NO.15)

PMAL3 (23mer): 5'-ACTTCTAGAATTTCATTATTTAT-3'
(SEQ ID NO.16)

Each of primers PMAL1 and PMAL2 had a NotI site at the 5' end (underlined). Primer PMAL1 contained the 3' terminal sequence of the AOD promoter, and PMAL2 contained the 5' terminal sequence of the AOD terminator. Primer PMAL3 contained a XbaI site located within the AOD terminator (underlined).

Plasmid pMOX330 containing the AOD promoter was mixed with primers PMAL1 and PMAL3, and a PCR was conducted. The reaction product thus obtained was electrophoresed on an agarose gel and the amplified DNA fragment was recovered. The recovered fragment (PN3 fragment) comprised the AOD promoter region downstream from the XbaI site, as well as a NotI site at the 3'-end.

Meanwhile, plasmid pMOX078 containing the AOD terminator, was mixed with primers PMAL2 and NP (see Example 1), and a PCR was conducted. The reaction product thus obtained was electrophoresed on an agarose gel and the amplified DNA fragment was recovered. The recovered fragment (TN fragment) comprised the AOD terminator upstream from the HindIII site as well as a NotI site at the 5'-end. Plasmid pMOX330 containing the AOD promoter was digested with EcoRI and XbaI and the product was electrophoresed on an agarose gel to recover a DNA fragment (PN5 fragment) which contained the AOD promoter region upstream from the XbaI site.

(2) Construction of expression vector

PN3 fragment resulting from the digestion with NotI and XbaI, TN fragment resulting from the digestion with NotI and HindIII, and vector pUC18 digested with XbaI and HindIII were ligated together by T4 DNA ligase to prepare the plasmid pPN1. This plasmid was then treated with EcoRI/XbaI and PN5 fragment was inserted to give the plasmid pNOT1. From plasmid pRCU350 containing URA3 gene of *Candida boidinii*, the URA3 fragment was excised with SalI and the fragment was blunt-ended with T4 DNA polymerase. Then the fragment was inserted into the NdeI site of plasmid pNOT1 to prepare the plasmid pNOTe1. Since the vector pNOTe1 contained, between the EcoRI site and the HindIII site from plasmid pUC18, an expression cassette consisting of AOD promoter/terminator, any desired heterologous gene can be inserted into the NotI site located between AOD promoter and AOD terminator. In addition, vector pNOTe1 contained at the NdeI site a URA 3 gene which was required for transformation of methylotrophic yeasts and integration of the cassette into a chromosomal DNA (see FIG. 6).

(3) Construction of expression vector for cytochrome C552

The methods for obtaining cytochrome C552 (Cyt552) gene and the nucleotide sequence of said gene are disclosed by Sanbongi et al. [Sanbongi, Y., Yang, J. H., Igarashi, Y. and Kodama, T., Eur. J. Biochem., 198, 7–12 (1991)]. From plasmid pKHC12 which contained the structural gene of Cyt552 at the EcoRI site of vector pUC18, a fragment containing said gene was excised with EcoRI and SalI and the fragment was blunt-ended with T4 DNA polymerase. Then the fragment was inserted into plasmid pNOTe1 which had been digested with NotI and blunt-ended, whereby the plasmid pNOTe1C552 for expressing CytC552 was obtained.

(4) Transformation and production of Cytochrome C

Transformation was carried out in a manner similar to that disclosed in Example 2. Also, the conditions for culturing the transformant and the medium etc. were similar to those in Example 2.

One strain (1-a strain) among transformants and the parent strain (TK62 strain) thereof were cultured in a medium containing methanol and/or glycerol as a carbon source, and the amount of cytochrome C expression in the cells was determined. The amount of cytochrome C expression was calculated by measuring the absorbance at 552 nm. After 100 hours in the methanol medium, 1-a strain produced 0.8 mg of cytochrome C552 per ml of the medium. This expression was not induced by the glucose medium. In the parent strain, the expression was not induced by a combination of the methanol medium and the glucose medium, indicating that the expression of the cytochrome C552 was induced by methanol.

EXAMPLE 6

This example shows isolation of the autonomously replicating sequence (ARS) of a methylotrophic yeast *Candida boidinii*, determination of the nucleotide sequence of ARS, and construction of plasmids which are capable of replicating in host cells by virtue of ARS.

(1) Isolation of ARS

Isolation of ARS was conducted by screening a gene library of *Candida boidinii* in accordance with the known method. The gene library of *Candida boidinii* was prepared in accordance with the method of Sakai et al. (Sakai, Y., Kazarimoto, T. and Tani, Y., J. Bacteriol., 173, 7458–7463 (1991)).

The screening of plasmids with ARS was conducted as follows. Chromosomal DNA from *Candida boidinii* was extensively digested with EcoRI or HindIII and the fragments were inserted in the EcoRI or the HindIII site of the plasmid pBCU351 (Sakai, Y., Kazarimoto, T. and Tani, Y., J. Ferment. Bioeng., 73, 255–260 (1992)) which contained URA3 of *Candida boidinii*. *E. coli* JM109 strain was transformed with these plasmids, and screening was conducted for transformants which contained ARS in the plasmid, with uracyl non-dependency as the measure. From the resulting 350 methylotrophic yeast transformants, plasmids were recovered to be used to transform *Candida boidinii*. Plasmids were prepared from the transformants and screened once more on the basis of uracyl non-dependency. The process of transforming *E. coli* JM109 strain and returning the screened plasmids back into *Candida boidinii* was repeated 3 times. The resulting 28 plasmids contained DNA sequences with strong ARS activities. The analyses given below were conducted using the two of these plasmids, pBARCU1 and pBARCU2, respectively containing a DNA sequence CARS1 or CARS2 with the strong ARS activity (FIGS. 8A, 8B, 8C and 8D).

(2) Construction of ARS-containing plasmids and resulting transformation efficiency The Plasmids used to transform *Saccharomyces cerevisiae* were constructed as follows. Plasmids pBARCU1 and pBARCU2 obtained in (1) in this example were treated with HindIII or EcoRI to give DNA fragments containing CARS1 or CARS2, respectively. The DNA fragments were inserted at the HindIII or the EcoRI site of YIp vector containing URA3 gene of *Saccharomyces cerevisiae*. The method for isolating the marker gene URA3 of *Candida boidinii* and the method for preparing the plasmids containing CARS1 or CARS2 are given in (1) in this example. The illustrative constructions of the resulting 4 plasmids, pBARCU1, pBARCU2, pRAC1 and pRAC2 are shown in FIGS. 8A, 8B, 8C and 8D.

Table 2 shows the transformation efficiencies observed when the hosts of *Candida boidinii* and *Saccharomyces cerevisiae* were transformed with the 4 plasmids. In the case of *Candida boidinii*, the host was transformed at higher efficiencies with these plasmids whereas the control plasmid without ARS did not produce transformants. In *Saccharomyces cerevisiae*, the transformation efficiencies were even higher than in *Candida boidinii*. A certain number of *Saccharomyces cerevisiae* transformants were formed by the control plasmid pBCU351, suggesting that the marker gene URA3 of *Candida boidinii* in the plasmid served as an ARS in *Saccharomyces cerevisiae*.

TABLE 2

Transformation efficiencies in uracyl requiring *C. boidinii* and *S. cerevisiae* strains when transformed with ARS-containing plasmids.

| Plasmid | marker gene | replication origin | transformation efficiency colony number/mg DNA | |
|---|---|---|---|---|
| | | | *C. boidinii* | *S. cerevisiae* |
| pBCU351 | *C. boidinii* URA3 | — | <1 | $4.5 \times 10^4$ |
| pBARCU1 | *C. boidinii* | CARS1 | $1.0 \times 10^4$ | $7.5 \times 10^4$ |

TABLE 2-continued

Transformation efficiencies in uracyl requiring *C. boidinii* and *S. cerevisiae* strains when transformed with ARS-containing plasmids.

| Plasmid | marker gene | replication origin | transformation efficiency colony number/mg DNA | |
|---|---|---|---|---|
| | | | *C. boidinii* | *S. cerevisiae* |
| pBARCU2 | *C. boidinii* URA3 | CARS2 | $5.0 \times 10^3$ | $6.1 \times 10^4$ |
| pRS406 | *S. cerevisiae* URA3 | — | <1 | <1 |
| pRAC1 | *S. cerevisiae* URA3 | ARS11 | $4.0 \times 10^2$ | $1.3 \times 10^5$ |
| pARC2 | *S. cerevisiae* URA3 | CARS2 | $1.0 \times 10^2$ | $7.1 \times 10^4$ |
| pYCU350 | *C. boidinii* URA3 | ARS1 | <1 | $1.0 \times 10^4$ |
| YEp24 | *S. cerevisiae* URA3 | 2 μm DNA | <1 | n.t. |

The results indicated that the vectors containing CARS1 or CARS2 increase transformation efficiency of *C. boidinii* and thus enable one to construct heterologous gene expression systems in these host cells. Further, these vectors can be employed as shuttle vectors between *C. boidinii* and *S. cerevisiae* since they are able to transform the two yeast species.

(3) Nucleotide sequence of ARS

The full nucleotide sequence of the above obtained DNA fragment which comprised CARS1 was determined in accordance with the known method of Sanger et al. (Sanger, F., Nicklen, S. and Coulson, A. R., Proc. Natl. Acad. Sci., 74, 5463–5467 (1977)). The clarified nucleotide sequence of CARS1 is shown in FIG. 7 (SEQ ID NO.4). The box in the figure indicates the portion which was similar to the consensus sequence in the ARS derived from *S. cerevisiae* (5'-(A/T)TTTATRTTT(A/T)-3'), while the underline indicates the portion which was similar to the ARS box from *S. cerevisiae* (5'-TNTRAA-3').

(4) Analysis of the functional sites in ARS

The functional sites in CARS1 of *C. boidinii* and *S. cerevisiae* were studied. Thus, restriction enzymes and a nuclease were used to prepare various deletion plasmids from plasmid pRAC1 having ARS function and plasmid pRAC1R containing CARS1 in the reverse orientation. FIG. 9 shows the transformation efficiencies in *C. boidinii* and *S. cerevisiae* hosts when the hosts were transformed with the deletion plasmids. The minimum sequence required to exhibit ARS function in *C. boidinii* comprised base Nos. 1–495 whereas that in *S. cerevisiae* comprised base Nos. 693–850.

EXAMPLE 7

This example illustrates production of a peroxidase by utilizing a transformed *Candida boidinii* having the expression cassette for the peroxidase gene which was integrated in the expression vector constructed in Example 5 having a NotI site between the promoter and the terminator of the alcohol oxidase (AOD) gene.

(1) Preparation of expression plasmid for *Arthromyces ramosus* peroxidase

The method for obtaining the peroxidase gene from *Arthromyces ramosus* (ARP) and the nucleotide sequence thereof are disclosed in Japanese Patent Public Disclosure No. 228078/92 (corresponds to EP 0486067). The DNA fragment containing the ARP gene was amplified by polymerase chain reactions (PCR) using the expression plasmid pYEPOD1 (Japanese Patent Disclosure No. 228078/92) having a cDNA of ARP gene as a template, and synthetic oligonucleotides A664 (5'-AAGCGGCCGCATGAAGCTCTCGCTTTTCTCCA-3' (SEQ ID NO. 17)) and A663 (5'-GTGCGGCCGCAGGATGTACCATCTTCACCAGA-3' (SEQ ID NO.18) as primers. The reaction product thus obtained was electrophoresed on an agarose gel and the amplified DNA fragment was recovered. The amplified DNA fragment comprises the ARP gene and two NotI sites at the 5'-end (adjacent to the initiation codon) and the 3'-end (21 bp downstream from the termination codon TGA). The DNA fragment was digested with NotI and inserted into the NotI site of plasmid pNOTe1 to construct the plasmid pNOTeIARP expressing ARP.

(2) Transformation and production of ARP

Transformation was carried out in a manner similar to that disclosed in Example 2. The method for culturing the transformant and the culture medium, etc. were substantially the same as disclosed in Example 3.

The transformant (AP-1 strain) and its parent strain (TK62 strain) were cultured in a medium containing methanol as the major carbon source for 100 hours. Then, the cells were recovered and the peroxidase activity in the supernatant of the culture was measured. The measurement of the peroxidase activity was carried out as disclosed in Japanese Patent Public Disclosure No. 228078/92. As a result, the peroxidase activity of AP-1 strain and TK62 strain were 137 u/l and 0.6 u/l, respectively. Accordingly, it was indicated that the active form of ARP was expressed in AP-1 strain and secreted in the medium.

What is claimed is:

1. A methanol and/or glycerol inducible expression cassette which comprises a promoter having the nucleotide sequence represented by SEQ. I.D. No. 1; a heterologous gene downstream of said promoter; and a terminator having the nucleotide sequence represented by SEQ. I.D. No. 2 downstream of said heterologous gene.

2. An expression vector having the expression cassette of claim 1.

3. The expression vector of claim 2, wherein said expression vector has a sequence portion homologous to a portion of the chromosomal DNA of host cells to integrate said cassette into the chromosomal DNA by a homologous recombination between the homologous sequence portions of the vector and the chromosome.

4. The expression vector of claim 2, wherein said expression vector has an autonomously replicating sequence represented by SEQ. I.D. No. 4.

5. A transformed cell which has been transformed with the expression vector as claimed in any one of claims 2 to 4.

6. A method for producing a peptide or a protein encoded by a heterologous gene comprising culturing said transformed cell of claim 5 in the presence of methanol and/or glycerol and isolating and purifying the desired peptide or protein which is an expression product of said heterologous gene from said culture.

7. The method of claim 6, wherein said heterologous gene is the gene which encodes the adenylate kinase derived from *Saccharomyces cerevisiae*.

8. The method of claim 6, wherein said heterologous gene is the gene which encodes the cytochrome C552 derived from *Hydrogenobacter thermophilus*.

9. The method of claim 6, wherein said heterologous gene is a gene which encodes the peroxidase derived from *Arthromyces ramosus*.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 1667 base pairs
        ( B ) TYPE: nucleic acid
        ( C ) STRANDEDNESS: double
        ( D ) TOPOLOGY: unknown (ii) MOLECULE TYPE: genomic DNA (iii) SEQUENCE DESCRIPTION: SEQ I.D. NO: 1:

| | | | | | | |
|---|---|---|---|---|---|---|
| GAATTCCGGA | GTATACGTAA | ATATATAATT | ATATATAATC | ATATATATGA | ATACAATGAA | 60 |
| AGTAAATATG | ATAAGATTGA | AATAATAACA | AACAGCGATA | AATATATCTC | AAAATGGAGT | 120 |
| TACACAACAA | ATAATAATAA | AATATAAATT | ATAAATATA | AAGGAATAAA | ATAAACCCCA | 180 |
| CTAATTTATT | TTATTAAAAG | ATAGATTGGT | ATCTTTACTT | AATAACAATT | CTGAAACTTT | 240 |
| ATTCACTTAA | TTTTATTTAA | CTTATTTAAT | TTATTTTTAC | CCCAGTTTTT | TCAGTACAGT | 300 |
| GCAGCTCCGA | AACTTTATTT | GGCTGTGATT | TGGCTGTGAT | TTGGCTTGGC | TTGGCTGGCT | 360 |
| GGAATTGTCT | CCTGCAGGAA | TTGCTCGGGG | TCCGGTTCTC | CCGCAGCTGG | ATATTTGGCT | 420 |
| GGCTGCTCTG | TCTGGCTGCT | CTGCCATCTG | CTGTGGCCAC | CCCCGCATCT | CTGGATGCAC | 480 |
| GCCGTGCAGC | TGGACTTGCG | TCTACCCTGC | AGCCGTGTGC | CTCATCTCCC | AATCTCTCAA | 540 |
| TCAGCCAGTC | AGCCAGCCAG | CCAAAATACG | GGCCAGGCAG | GCAGGCAGGC | AGGCAGGCAG | 600 |
| GCAGGCAGGC | AGGCAGGCAG | GCAGTGATGC | CTTCCCACGC | CCCACCCCGC | ATAAACATCC | 660 |
| CCAGCAGTTT | CCCCAGCAGT | TCCCCAGCT | TTTCAATTTA | ATAAAATAGC | CTGTTTCTGT | 720 |
| TTCTGTTTTA | TATTATACAA | TTTTTATCC | TAATAATTAC | TCTTTGGGA | ATTAAATAAT | 780 |
| AATTATATCA | TATACCCATA | TCACATTTTA | CTATATTTAC | TATCTATAAA | TAATTTCATA | 840 |
| TTATAATATT | AATTTATATT | CGCTTAATTA | AAATGCTCTT | TTCCATCATC | ATCATCATCA | 900 |
| TCATCACGAG | TTTTCGGTTA | TCAATACTCT | TTTCATTAAC | TTCTAGAATT | TCATTATTTA | 960 |
| TTTTTTATTG | ACTGGAAATT | TTCAATCAAT | TTATTTATT | TTATTTATT | TATTTTCATA | 1020 |
| TTCTTAGATT | TAAACTTTTT | AGATGACCGC | TATTTTACTT | ACTTACTTAC | TTACTTACTT | 1080 |
| ACTTACTTAC | TTACATACCT | ACTTACTGTG | ATTTATAAT | ATGATAAGAA | TTAATTTTCA | 1140 |
| TATTTATGAT | GATGTAAATT | TAACCTAGTA | TACTATTTTA | AAGTTATCAC | TATCTTTTAG | 1200 |
| TGCTGGCATT | TTTTATTCTA | TTTTCATATA | TGTATATAAG | TAAATTAAGT | ATCATCACGC | 1260 |
| TGCTTACTGT | ACGTTAAAA | TGTGGAGATG | GAAATAGAGA | TGGGGATGAA | GATGAAGATG | 1320 |
| ATGAGAATTA | TAAACCATTC | ATTCATTAAT | CAATCAATAT | AACTTATAAA | AAAATTTATA | 1380 |
| TTTAAATGAA | TTAATTTCCT | TTATTTTAAT | AATATCGTTA | ATTCTTTTAA | ATTCTATTTT | 1440 |
| ATTTTAATTC | TTTCTTTATC | ATAGTTATCA | TATAACAATT | ATATAACATA | GATACACAAT | 1500 |
| TATTATTTTA | TTATCATATT | ATTTTTAAA | ATATTGATTA | TTTTAAAAT | AATATCTTAA | 1560 |
| TTAATTAATT | TTTACGAATA | TACAAATTTT | AACGACTTTC | TTTTTTAAC | GAATTTAAC | 1620 |
| GAACTTTTAA | AAAACAAAA | AAAAAAAAC | AAAATTATTT | TTCAATA | | 1667 |

(2) INFORMATION FOR SEQ ID NO:2:

(i) SEQUENCE CHARACTERISTICS:
        (A) LENGTH: 518 base pairs
        (B) TYPE: nucleic acid
        (C) STRANDEDNESS: double
        (D) TOPOLOGY: unknown (ii) MOLECULE TYPE: genomic DNA (iii) SEQUENCE DESCRIPTION: SEQ I.D. NO: 2:

| | | | | | | |
|---|---|---|---|---|---|---|
| TAATTCAACA | AGTTGTATCT | TTTTTACTG | CTCTTTTTA | ATGATCTCTC | TTTATTTTT | 60 |
| TTTCAATCAA | TTTATTTATT | TAATTTTTTC | ACTTTTATAA | TTCTTGATAT | GATATGATAT | 120 |
| GATATGATTT | TAGTTCTTTG | TCTGTTTTT | TTTTTTTTT | TCAAACTTTT | CTTTTAATGA | 180 |
| CTTTATACCA | AAAATTTTCA | AAAATTTCCA | AAAAAAAAA | CAATAATGTT | CTTTTTACGT | 240 |

-continued

```
CTCTTTCCTT TTACAAAATA TATTTATTGC CTGCCTCATT TTTTTCAAAT ACTTTTTTTT        300

CCCTGTAACA GTAATTAGTA AATTGAAAAA AATAATTATT AATTTAAGTA AATAGCAGCA        360

ACATTGAGGT TTACAAATAT AGTAATAATA GTCTATCTAC AACCAATATT AAATAATTTG        420

ATCATTTAAA ACAACATTAA ATTTGAAATT TAGTACATAA TTAATAAAAG AAAAGAGGAG        480

AAACAAAAGC ATAATAAATC ATTAAAATTT GAGTATAG                                518
```

( 2 ) INFORMATION FOR SEQ ID NO:3:

( i ) SEQUENCE CHARACTERISTICS:
        ( A ) LENGTH: 1992 base pairs
        ( B ) TYPE: nucleic acid
        ( C ) STRANDEDNESS: double
        ( D ) TOPOLOGY: unknown ( i i ) MOLECULE TYPE: genomic DNA ( i i i ) SEQUENCE DESCRIPTION: SEQ I.D. NO: 3:

```
ATG GCT ATC CCA GAA GAA TTT GAC GTT ATT GTT TGT GGT GGT GGT TCC         48
Met Ala Ile Pro Glu Glu Phe Asp Val Ile Val Cys Gly Gly Gly Ser
 1               5                  10                  15

ACT GGT TGT GTT ATT GCA GGT CGT CTT GCA AAT GTC GAT GAA AAT TTA         96
Thr Gly Cys Val Ile Ala Gly Arg Leu Ala Asn Val Asp Glu Asn Leu
            20                  25                  30

AAA GTT TTA TTG ATT GAA AAT GGT GAA AAT AAT TTA AAT AAT CCA TGG        144
Lys Val Leu Leu Ile Glu Asn Gly Glu Asn Asn Leu Asn Asn Pro Trp
        35                  40                  45

GTT TAT TTA CCA GGT ATT TAT CCA AGA AAT ATG AGA TTA GAT TCA AAA        192
Val Tyr Leu Pro Gly Ile Tyr Pro Arg Asn Met Arg Leu Asp Ser Lys
    50                  55                  60

ACT GCA ACT TTT TAT AAT TCA AGA CCA TCA AAA CAT TTA AAT GGT CGT        240
Thr Ala Thr Phe Tyr Asn Ser Arg Pro Ser Lys His Leu Asn Gly Arg
65                  70                  75                  80

CGT GCT ATT GTT CCT CAA GCT AAT ATC TTA GGT GGT GGT TCA TCT ATT        288
Arg Ala Ile Val Pro Gln Ala Asn Ile Leu Gly Gly Gly Ser Ser Ile
                85                  90                  95

AAT TTT ATG ATG TAT ACA AGA GCT TCT GCT TCT GAT TAT GAT GAT TGG        336
Asn Phe Met Met Tyr Thr Arg Ala Ser Ala Ser Asp Tyr Asp Asp Trp
            100                 105                 110

GAA TCT GAA GGT TGG ACT ACT GAT GAA TTA TTA CCA TTG ATG AAA AAA        384
Glu Ser Glu Gly Trp Thr Thr Asp Glu Leu Leu Pro Leu Met Lys Lys
        115                 120                 125

TTT GAA ACT TAT CAA CGT CCT TGT AAT AAC AGA GAT GTT CAT GGT TTT        432
Phe Glu Thr Tyr Gln Arg Pro Cys Asn Asn Arg Asp Val His Gly Phe
    130                 135                 140

GAT GGT CCA ATT AAA GTT TCT TTT GGT AAT TAT ACT TAT CCT CAA TGT        480
Asp Gly Pro Ile Lys Val Ser Phe Gly Asn Tyr Thr Tyr Pro Gln Cys
145                 150                 155                 160

CAA GAT TTC CTT AGA GCT TGT GAA ACA CAA GGT ATC CCA TAC GTT GAT        528
Gln Asp Phe Leu Arg Ala Cys Glu Thr Gln Gly Ile Pro Tyr Val Asp
                165                 170                 175

GAT TTA GAA GAT TTG AAA ACT TCT CAT GGT GCT GAA CAA TGG TTA AAA        576
Asp Leu Glu Asp Leu Lys Thr Ser His Gly Ala Glu Gln Trp Leu Lys
            180                 185                 190

TGG ATT AAC AGA GAT TTT GGT AGA CGT TCT GAT ACT GCT CAT GCT TTT        624
Trp Ile Asn Arg Asp Phe Gly Arg Arg Ser Asp Thr Ala His Ala Phe
        195                 200                 205

ATT CAT TCA ACT ATG AGA AAT AAA GAA AAT TTA TTT TTA ATG ACT AAT        672
Ile His Ser Thr Met Arg Asn Lys Glu Asn Leu Phe Leu Met Thr Asn
    210                 215                 220

ACT AAA GTT GAT AAA GTT ATT ATT GAA GAT GGT AGA GCA GTT GCA GTT        720
```

| | | | | | | | | | | | | | | | | |
|---|---|---|---|---|---|---|---|---|---|---|---|---|---|---|---|---|
| Thr | Lys | Val | Asp | Lys | Val | Ile | Ile | Glu | Asp | Gly | Arg | Ala | Val | Ala | Val | |
| 225 | | | | 230 | | | | | 235 | | | | | 240 | | |
| AGA | ACC | GTT | CCA | TCA | AAA | CCA | ATT | GGT | GAT | TCT | AAA | GTT | TCA | AGA | ACT | 768 |
| Arg | Thr | Val | Pro | Ser | Lys | Pro | Ile | Gly | Asp | Ser | Lys | Val | Ser | Arg | Thr | |
| | | | | 245 | | | | | 250 | | | | | 255 | | |
| TTT | AAA | GCT | AGA | AAA | CAA | ATT | GTT | GTT | TCT | TGT | GGT | ACT | GTT | TCT | TCT | 816 |
| Phe | Lys | Ala | Arg | Lys | Gln | Ile | Val | Val | Ser | Cys | Gly | Thr | Val | Ser | Ser | |
| | | | 260 | | | | | 265 | | | | | 270 | | | |
| CCA | ATG | GTT | TTA | CAA | AGA | TCT | GGT | ATT | GGT | GAA | CCA | TCT | AAA | TTA | AGA | 864 |
| Pro | Met | Val | Leu | Gln | Arg | Ser | Gly | Ile | Gly | Glu | Pro | Ser | Lys | Leu | Arg | |
| | | 275 | | | | | 280 | | | | | 285 | | | | |
| GCT | GCT | GGT | GTT | AAA | CCA | ATT | GTT | GAA | TTA | CCA | GGT | GTT | GGT | AGA | AAT | 912 |
| Ala | Ala | Gly | Val | Lys | Pro | Ile | Val | Glu | Leu | Pro | Gly | Val | Gly | Arg | Asn | |
| | | 290 | | | | | 295 | | | | | 300 | | | | |
| TTC | CAA | GAT | CAT | TTC | TGT | TAT | TTC | GTT | CCA | TAT | AGA | ATC | AAA | CAA | GAT | 960 |
| Phe | Gln | Asp | His | Phe | Cys | Tyr | Phe | Val | Pro | Tyr | Arg | Ile | Lys | Gln | Asp | |
| 305 | | | | 310 | | | | | 315 | | | | | 320 | | |
| TCT | GAA | TCA | TTC | GAT | GCA | TTT | GTC | TCT | GGT | GAT | AAA | GAA | GCT | CAA | AAA | 1008 |
| Ser | Glu | Ser | Phe | Asp | Ala | Phe | Val | Ser | Gly | Asp | Lys | Glu | Ala | Gln | Lys | |
| | | | | 325 | | | | | 330 | | | | | 335 | | |
| TCA | GCT | TTT | GAT | CAA | TGG | TAT | GCT | ACA | GGT | GCT | GGT | CCA | TTA | GCT | ACA | 1056 |
| Ser | Ala | Phe | Asp | Gln | Trp | Tyr | Ala | Thr | Gly | Ala | Gly | Pro | Leu | Ala | Thr | |
| | | | 340 | | | | | 345 | | | | | 350 | | | |
| AAT | GGT | ATT | GAA | GCT | GGT | GTT | AAA | ATT | AGA | CCA | ACA | GAA | GCT | GAA | TTG | 1104 |
| Asn | Gly | Ile | Glu | Ala | Gly | Val | Lys | Ile | Arg | Pro | Thr | Glu | Ala | Glu | Leu | |
| | | 355 | | | | | 360 | | | | | 365 | | | | |
| GCA | ACT | GCT | GAT | AAG | GCT | TTC | CAA | CAA | GGT | TGG | GAA | TCT | TAT | TTT | GAA | 1152 |
| Ala | Thr | Ala | Asp | Lys | Ala | Phe | Gln | Gln | Gly | Trp | Glu | Ser | Tyr | Phe | Glu | |
| | 370 | | | | | 375 | | | | | 380 | | | | | |
| AAT | AAA | CCA | GAT | AAA | CCA | TTA | ATG | CAT | TAT | TCT | GTT | ATT | TCA | GGT | TTC | 1200 |
| Asn | Lys | Pro | Asp | Lys | Pro | Leu | Met | His | Tyr | Ser | Val | Ile | Ser | Gly | Phe | |
| 385 | | | | | 390 | | | | | 395 | | | | | 400 | |
| TTT | GGT | GAT | CAC | ACT | AGA | TTA | CCA | CCA | GGA | AAA | TAT | ATG | ACT | ATG | TTC | 1248 |
| Phe | Gly | Asp | His | Thr | Arg | Leu | Pro | Pro | Gly | Lys | Tyr | Met | Thr | Met | Phe | |
| | | | | 405 | | | | | 410 | | | | | 415 | | |
| CAT | TTC | TTA | GAA | TAT | CCA | TTC | TCA | AGA | GGT | TGG | TTA | CAC | ATT | TCA | TCT | 1296 |
| His | Phe | Leu | Glu | Tyr | Pro | Phe | Ser | Arg | Gly | Trp | Leu | His | Ile | Ser | Ser | |
| | | | 420 | | | | | 425 | | | | | 430 | | | |
| GAT | GAT | CCA | TAT | GCT | GCT | CCA | GAT | TTC | GAT | CCA | GGT | TTT | ATG | AAT | GAT | 1344 |
| Asp | Asp | Pro | Tyr | Ala | Ala | Pro | Asp | Phe | Asp | Pro | Gly | Phe | Met | Asn | Asp | |
| | | 435 | | | | | 440 | | | | | 445 | | | | |
| GAC | AGA | GAT | ATG | TGG | CCA | ATG | GTT | TGG | GCA | TTC | AAG | AAA | TCA | AGA | GAA | 1392 |
| Asp | Arg | Asp | Met | Trp | Pro | Met | Val | Trp | Ala | Phe | Lys | Lys | Ser | Arg | Glu | |
| | 450 | | | | | 455 | | | | | 460 | | | | | |
| ACC | GCT | AGA | AGA | ATG | GAA | TGT | TTT | GCT | GGT | GAA | CCA | ACA | GCT | TTC | CAT | 1440 |
| Thr | Ala | Arg | Arg | Met | Glu | Cys | Phe | Ala | Gly | Glu | Pro | Thr | Ala | Phe | His | |
| 465 | | | | | 470 | | | | | 475 | | | | | 480 | |
| CCA | CAT | TAT | AAA | GTT | GAT | TCT | CCT | GCT | AGA | GCT | TTA | GAA | CAA | AGT | GCT | 1488 |
| Pro | His | Tyr | Lys | Val | Asp | Ser | Pro | Ala | Arg | Ala | Leu | Glu | Gln | Ser | Ala | |
| | | | | 485 | | | | | 490 | | | | | 495 | | |
| GAA | GAT | ACT | AAG | AAA | GTT | GCT | GGT | CCA | CTT | CAC | TTA | ACT | GCT | AAC | TTG | 1536 |
| Glu | Asp | Thr | Lys | Lys | Val | Ala | Gly | Pro | Leu | His | Leu | Thr | Ala | Asn | Leu | |
| | | | 500 | | | | | 505 | | | | | 510 | | | |
| TAT | CAC | GGT | TCT | TGG | TCT | ACT | CCA | ATT | GGT | GAA | GCT | GAT | AAA | CAT | GAT | 1584 |
| Tyr | His | Gly | Ser | Trp | Ser | Thr | Pro | Ile | Gly | Glu | Ala | Asp | Lys | His | Asp | |
| | | 515 | | | | | 520 | | | | | 525 | | | | |
| CCA | AAT | CAT | GTT | ACT | TCT | TCT | CAT | ATT | AAC | GTT | TAC | TCT | AAG | GAT | ATT | 1632 |
| Pro | Asn | His | Val | Thr | Ser | Ser | His | Ile | Asn | Val | Tyr | Ser | Lys | Asp | Ile | |
| | 530 | | | | | 535 | | | | | 540 | | | | | |
| CAA | TAC | ACA | AAA | GAA | GAT | GAT | GAA | GCT | ATT | GAA | AAT | TAC | ATT | AAG | GAA | 1680 |

| | | | | | | | | | | | | | | | | |
|---|---|---|---|---|---|---|---|---|---|---|---|---|---|---|---|---|
| Gln<br>545 | Tyr | Thr | Lys | Glu | Asp<br>550 | Asp | Glu | Ala | Ile | Glu<br>555 | Asn | Tyr | Ile | Lys | Glu<br>560 | |
| CAC | GCT | GAA | ACT | ACA | TGG | CAT | TGT | CTT | GGT | ACT | AAC | TCC | ATG | GCT | CCA | 1728 |
| His | Ala | Glu | Thr | Thr<br>565 | Trp | His | Cys | Leu | Gly<br>570 | Thr | Asn | Ser | Met | Ala<br>575 | Pro | |
| AGA | GAA | GGT | AAT | AAG | AAT | GCT | CCA | GAA | GGT | GGT | GTC | TTG | GAT | CCA | AGA | 1776 |
| Arg | Glu | Gly | Asn<br>580 | Lys | Asn | Ala | Pro | Glu<br>585 | Gly | Gly | Val | Leu | Asp<br>590 | Pro | Arg | |
| TTA | AAC | GTT | CAT | GGT | GTT | AAG | GGA | TTA | AAA | GTT | GCT | GAT | TTA | TCA | GTT | 1824 |
| Leu | Asn | Val<br>595 | His | Gly | Val | Lys | Gly<br>600 | Leu | Lys | Val | Ala | Asp<br>605 | Leu | Ser | Val | |
| TGT | CCA | GAT | AAT | GTT | GGT | TGT | AAT | ACT | TTC | TCA | ACT | GCT | TTA | ACT | ATT | 1872 |
| Cys | Pro<br>610 | Asp | Asn | Val | Gly | Cys<br>615 | Asn | Thr | Phe | Ser | Thr<br>620 | Ala | Leu | Thr | Ile | |
| GGT | GAA | AAA | GCT | GCA | GTT | TTA | GTA | GCT | GAA | GAT | TTA | GGT | TAC | TCT | GGT | 1920 |
| Gly<br>625 | Glu | Lys | Ala | Ala | Val<br>630 | Leu | Val | Ala | Glu | Asp<br>635 | Leu | Gly | Tyr | Ser | Gly<br>640 | |
| TCT | GAA | TTA | GAT | ATG | GAA | GTT | CCA | CAA | CAT | AAA | TTA | AAA | ACT | TAT | GAA | 1968 |
| Ser | Glu | Leu | Asp | Met<br>645 | Glu | Val | Pro | Gln | His<br>650 | Lys | Leu | Lys | Thr | Tyr<br>655 | Glu | |
| CAA | ACT | GGT | GCT | GCT | CGT | TAT | TAA | | | | | | | | | 1992 |
| Gln | Thr | Gly | Ala<br>660 | Ala | Arg | Tyr | STP | | | | | | | | | |

(2) INFORMATION FOR SEQ ID NO:4:

(i) SEQUENCE CHARACTERISTICS:
        (A) LENGTH: 850 base pairs
        (B) TYPE: nucleic acid
        (C) STRANDEDNESS: double
        (D) TOPOLOGY: unknown (ii) MOLECULE TYPE: genomic DNA (iii) SEQUENCE DESCRIPTION: SEQ I.D. NO: 4:

```
AAGCTTTTTA TCACTAGTGA AATTAGTGAT TATAATGATA TAATCAAAAA TAGTACCTTG     60
GATGAGAAAA GCATTGTGTT TAATATTTAT GTATTGCACT ACACTCAATA GGACCGTGCG    120
AGGCAGTCTA AGAGATCCAC AAAATTTATG TAAATGATAT TATCACGTGA TATTAATGAA    180
ACATTTTAAT TGTTGTTTTT GCGTCGAGTT ATCAACTGAC TTCTTATGTA CTTTGTGACT    240
ATATAGATTT TGAGTAGTAT TAAGTATTTC TCAGCGCGTA ATAATCAGTG TTGGTCTACC    300
AGCTAATTAT TACTATATGA TCTCTATGAT ACGATATTCT GAGAAATGAT TAATAAGCGT    360
TAATATGCAT ACAATAACAA AATGATTTAT ATTAATTAAT AACAAAGTTA TAAAGTAAAT    420
AAATATAATA AATACAATTG AATAAAATAA GATAAGTAAG ATAGATCTCT TTTCTATTCG    480
TTATGAACTT ATAACAAACA GTAAGAGTTA AAAGGATATA GATTTATATA TATAAAAGAG    540
TAAACTATAT AGAAGGTAGT GTACTAATGC TAAGTAAACT AATCCTAAAT AAGTTGAAAA    600
CTAATAAATA CGTTAAATCC GTACATTAGA AAGTAGTGTA ATAAACAATG TAGAAATGAA    660
CTAAAGTTCA TAATCTACAT TTATATGTAT TTATAAAAAT TCGCGTGACT TTAACTTAAG    720
ATAGATTATA GTTAAAACTG CTATAGAAAT AATATGTAAC AATTTTATGT TGTATACATT    780
TAATTATATT TAGTTTATAA AAATAAAGTA TATAGTGAAA AAGTGAATAA AAGTGAATAA    840
AATAAAGCTT                                                          850
```

(2) INFORMATION FOR SEQ ID NO:5:

(i) SEQUENCE CHARACTERISTICS:
        (A) LENGTH: 664 amino acids
        (B) TYPE: amino acid ( C ) STRANDEDNESS: double
( D ) TOPOLOGY: unknown ( i i ) MOLECULE TYPE: DNA (genomic)

( x i ) SEQUENCE DESCRIPTION: SEQ ID NO:5:

```
Met Ala Ile Pro Glu Glu Phe Asp Val Ile Val Cys Gly Gly Gly Ser
 1               5                  10                  15

Thr Gly Cys Val Ile Ala Gly Arg Leu Ala Asn Val Asp Glu Asn Leu
                20                  25                  30

Lys Val Leu Leu Ile Glu Asn Gly Glu Asn Asn Leu Asn Asn Pro Trp
            35                  40                  45

Val Tyr Leu Pro Gly Ile Tyr Pro Arg Asn Met Arg Leu Asp Ser Lys
        50                  55                  60

Thr Ala Thr Phe Tyr Asn Ser Arg Pro Ser Lys His Leu Asn Gly Arg
65                  70                  75                  80

Arg Ala Ile Val Pro Gln Ala Asn Ile Leu Gly Gly Gly Ser Ser Ile
                85                  90                  95

Asn Phe Met Met Tyr Thr Arg Ala Ser Ala Ser Asp Tyr Asp Asp Trp
                100                 105                 110

Glu Ser Glu Gly Trp Thr Thr Asp Glu Leu Leu Pro Leu Met Lys Lys
            115                 120                 125

Phe Glu Thr Tyr Gln Arg Pro Cys Asn Asn Arg Asp Val His Gly Phe
    130                 135                 140

Asp Gly Pro Ile Lys Val Ser Phe Gly Asn Tyr Thr Tyr Pro Gln Cys
145                 150                 155                 160

Gln Asp Phe Leu Arg Ala Cys Glu Thr Gln Gly Ile Pro Tyr Val Asp
                165                 170                 175

Asp Leu Glu Asp Leu Lys Thr Ser His Gly Ala Glu Gln Trp Leu Lys
                180                 185                 190

Trp Ile Asn Arg Asp Phe Gly Arg Arg Ser Asp Thr Ala His Ala Phe
            195                 200                 205

Ile His Ser Thr Met Arg Asn Lys Glu Asn Leu Phe Leu Met Thr Asn
    210                 215                 220

Thr Lys Val Asp Lys Val Ile Ile Glu Asp Gly Arg Ala Val Ala Val
225                 230                 235                 240

Arg Thr Val Pro Ser Lys Pro Ile Gly Asp Ser Lys Val Ser Arg Thr
                245                 250                 255

Phe Lys Ala Arg Lys Gln Ile Val Val Ser Cys Gly Thr Val Ser Ser
                260                 265                 270

Pro Met Val Leu Gln Arg Ser Gly Ile Gly Glu Pro Ser Lys Leu Arg
            275                 280                 285

Ala Ala Gly Val Lys Pro Ile Val Glu Leu Pro Gly Val Gly Arg Asn
    290                 295                 300

Phe Gln Asp His Phe Cys Tyr Phe Val Pro Tyr Arg Ile Lys Gln Asp
305                 310                 315                 320

Ser Glu Ser Phe Asp Ala Phe Val Ser Gly Asp Lys Glu Ala Gln Lys
                325                 330                 335

Ser Ala Phe Asp Gln Trp Tyr Ala Thr Gly Ala Gly Pro Leu Ala Thr
                340                 345                 350

Asn Gly Ile Glu Ala Gly Val Lys Ile Arg Pro Thr Glu Ala Glu Leu
            355                 360                 365

Ala Thr Ala Asp Lys Ala Phe Gln Gln Gly Trp Glu Ser Tyr Phe Glu
    370                 375                 380

Asn Lys Pro Asp Lys Pro Leu Met His Tyr Ser Val Ile Ser Gly Phe
```

```
                385                   390                   395                   400
        Phe  Gly  Asp  His  Thr  Arg  Leu  Pro  Pro  Gly  Lys  Tyr  Met  Thr  Met  Phe
                          405                       410                  415

His  Phe  Leu  Glu  Tyr  Pro  Phe  Ser  Arg  Gly  Trp  Leu  His  Ile  Ser  Ser
                          420                       425                  430

Asp  Asp  Pro  Tyr  Ala  Ala  Pro  Asp  Phe  Asp  Pro  Gly  Phe  Met  Asn  Asp
                          435                       440                  445

Asp  Arg  Asp  Met  Trp  Pro  Met  Val  Trp  Ala  Phe  Lys  Lys  Ser  Arg  Glu
             450                            455                  460

Thr  Ala  Arg  Arg  Met  Glu  Cys  Phe  Ala  Gly  Glu  Pro  Thr  Ala  Phe  His
        465                            470                       475                  480

Pro  His  Tyr  Lys  Val  Asp  Ser  Pro  Ala  Arg  Ala  Leu  Glu  Gln  Ser  Ala
                          485                       490                       495

Glu  Asp  Thr  Lys  Lys  Val  Ala  Gly  Pro  Leu  His  Leu  Thr  Ala  Asn  Leu
                          500                       505                       510

Tyr  His  Gly  Ser  Trp  Ser  Thr  Pro  Ile  Gly  Glu  Ala  Asp  Lys  His  Asp
                     515                       520                  525

Pro  Asn  His  Val  Thr  Ser  Ser  His  Ile  Asn  Val  Tyr  Ser  Lys  Asp  Ile
             530                       535                       540

Gln  Tyr  Thr  Lys  Glu  Asp  Asp  Glu  Ala  Ile  Glu  Asn  Tyr  Ile  Lys  Glu
        545                       550                       555                       560

His  Ala  Glu  Thr  Thr  Trp  His  Cys  Leu  Gly  Thr  Asn  Ser  Met  Ala  Pro
                          565                       570                       575

Arg  Glu  Gly  Asn  Lys  Asn  Ala  Pro  Glu  Gly  Gly  Val  Leu  Asp  Pro  Arg
                     580                       585                       590

Leu  Asn  Val  His  Gly  Val  Lys  Gly  Leu  Lys  Val  Ala  Asp  Leu  Ser  Val
                     595                       600                       605

Cys  Pro  Asp  Asn  Val  Gly  Cys  Asn  Thr  Phe  Ser  Thr  Ala  Leu  Thr  Ile
             610                       615                       620

Gly  Glu  Lys  Ala  Ala  Val  Leu  Val  Ala  Glu  Asp  Leu  Gly  Tyr  Ser  Gly
        625                            630                       635                       640

Ser  Glu  Leu  Asp  Met  Glu  Val  Pro  Gln  His  Lys  Leu  Lys  Thr  Tyr  Glu
                          645                       650                       655

Gln  Thr  Gly  Ala  Ala  Arg  Tyr  Xaa
                       660
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:6:

```
        Ala  Ile  Pro  Glu  Glu  Phe  Asp  Val  Ile  Val
        1                   5                        10
```

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:7:

TCRAGDGGRA TNGCCAT                                                                                   17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:8:

ACRATRACRT CRAAYTC                                                                                   17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:9:

ACRTCRAAYT CRAGDGG                                                                                   17

( 2 ) INFORMATION FOR SEQ ID NO:10:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:10:

GGATTCTGAA CTAGACATTA TTGAAAAATA ATTTTGT                                                              37

( 2 ) INFORMATION FOR SEQ ID NO:11:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:11:

ACAAAATTAT TTTCAATAA TGTCTAGTTC AGAATCC                                                               37

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:12:

GGAACTAGTT AATTCAACAA GTTGTATCT                                                                      29

( 2 ) INFORMATION FOR SEQ ID NO:13:

( i ) SEQUENCE CHARACTERISTICS:
      ( A ) LENGTH: 31 base pairs
      ( B ) TYPE: nucleic acid
      ( C ) STRANDEDNESS: double
      ( D ) TOPOLOGY: unknown ( i i ) MOLECULE TYPE: DNA (genomic)

( x i ) SEQUENCE DESCRIPTION: SEQ ID NO:13:

GGAACTAGTT CATTAATCCT TACCTAACTT G   31

( 2 ) INFORMATION FOR SEQ ID NO:14:

( i ) SEQUENCE CHARACTERISTICS:
      ( A ) LENGTH: 29 base pairs
      ( B ) TYPE: nucleic acid
      ( C ) STRANDEDNESS: unknown
      ( D ) TOPOLOGY: unknown ( i i ) MOLECULE TYPE: DNA (genomic)

( x i ) SEQUENCE DESCRIPTION: SEQ ID NO:14:

GGGCGGCCGC TATTGAAAAA TAATTTGT   29

( 2 ) INFORMATION FOR SEQ ID NO:15:

( i ) SEQUENCE CHARACTERISTICS:
      ( A ) LENGTH: 31 base pairs
      ( B ) TYPE: nucleic acid
      ( C ) STRANDEDNESS: double
      ( D ) TOPOLOGY: unknown ( i i ) MOLECULE TYPE: DNA (genomic)

( x i ) SEQUENCE DESCRIPTION: SEQ ID NO:15:

GGGCGGCCGC TAATTCAACA AAGTTGTATC T   31

( 2 ) INFORMATION FOR SEQ ID NO:16:

( i ) SEQUENCE CHARACTERISTICS:
      ( A ) LENGTH: 23 base pairs
      ( B ) TYPE: nucleic acid
      ( C ) STRANDEDNESS: double
      ( D ) TOPOLOGY: unknown ( i i ) MOLECULE TYPE: DNA (genomic)

( x i ) SEQUENCE DESCRIPTION: SEQ ID NO:16:

ACTTCTAGAA TTTCATTATT TAT   23

( 2 ) INFORMATION FOR SEQ ID NO:17:

( i ) SEQUENCE CHARACTERISTICS:
      ( A ) LENGTH: 32 base pairs
      ( B ) TYPE: nucleic acid
      ( C ) STRANDEDNESS: double
      ( D ) TOPOLOGY: unknown ( i i ) MOLECULE TYPE: DNA (genomic)

( x i ) SEQUENCE DESCRIPTION: SEQ ID NO:17:

AAGCGGCCGC ATGAAGCTCT CGCTTTTCTC CA   32

( 2 ) INFORMATION FOR SEQ ID NO:18:

( i ) SEQUENCE CHARACTERISTICS:
      ( A ) LENGTH: 32 base pairs
      ( B ) TYPE: nucleic acid

```
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:18:

GTGCGGCCGC  AGGATGTACC  ATCTTCACCA  GA                                            3 2
```